(12) United States Patent
Krasutsky et al.

(10) Patent No.: US 6,689,767 B2
(45) Date of Patent: Feb. 10, 2004

(54) TRITERPENES HAVING ANTIBACTERIAL ACTIVITY

(75) Inventors: Pavel A. Krasutsky, Duluth, MN (US); Robert M. Carlson, Duluth, MN (US); Raj Karim, Duluth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 143 days.

(21) Appl. No.: 09/969,556

(22) Filed: Oct. 1, 2001

(65) Prior Publication Data

US 2002/0119935 A1 Aug. 29, 2002

Related U.S. Application Data

(60) Provisional application No. 60/236,510, filed on Sep. 29, 2000.

(51) Int. Cl.$^7$ .............................................. A61K 31/56
(52) U.S. Cl. ..................................................... 514/169
(58) Field of Search ......................................... 514/169

(56) References Cited

U.S. PATENT DOCUMENTS

| | | | |
|---|---|---|---|
| 4,559,157 A | 12/1985 | Smith et al. ................... | 252/90 |
| 4,606,911 A | 8/1986 | Hayashi et al. ................ | 424/49 |
| 4,608,392 A | 8/1986 | Jacquet et al. ............... | 514/844 |
| 4,820,508 A | 4/1989 | Wortzman .................... | 424/59 |
| 4,938,949 A | 7/1990 | Borch et al. .................. | 424/10 |
| 4,992,478 A | 2/1991 | Geria ......................... | 514/782 |
| 5,190,979 A * | 3/1993 | Herman ....................... | 514/762 |
| 5,750,578 A | 5/1998 | Carlson et al. ............. | 514/766 |
| 5,883,074 A * | 3/1999 | Boggs et al. ................... | 514/8 |
| 6,303,589 B1 | 10/2001 | Glinski et al. .............. | 514/169 |

FOREIGN PATENT DOCUMENTS

| | | | |
|---|---|---|---|
| WO | WO-96/34005 | 10/1996 | ........... C07H/15/24 |
| WO | WO-97/03995 | 2/1997 | ........... C07H/15/24 |
| WO | WO-98/32443 | 7/1998 | ........... A61K/31/56 |
| WO | WO-00/24762 | 5/2000 | ........... C07J/63/00 |

OTHER PUBLICATIONS

*Aldrich Chemical Co. 2000–2001 Catalog*, p. 871.

*Merck Index, Twelfth ed.*, (1996), p. 1236.

Chen, X., et al., "Induction of Acquired Resistance in Bean Plants Against Pythium ultimum Fungal Infection by 9,10–epoxy, 18–hydroxy octadecanoic acid", *University of Minnesota Duluth, Sixteenth Annual Sigma XI–Duluth Scientific Poster Exhibition*, (Feb. 21, 2000), 1 page.

Gennaro, A.R., *Remington's Pharmaceutical Sciences*, Mack Pub. Co., 18th ed.,(1990), pp. 384–386.

Kahn, M. R., et al., "Antibiotic Action of Constituents of Root Bark of Euclea Natalensis A.DC.", *Pakistab J of Scientific Industrial Res.*, vol. 21, No. 5–6, XP000978450, (1979), pp. 197–199.

Keyel, P. A., et al., "In Vitro Effect Acyclovir, Betulin and Cyclodextrin Solutions with Different Ionic Strengths Against Herpes Simplex Virus Infections", *University of Minnesota Duluth, Sixteenth Annual Sigma XI–Duluth Scientific Poster Exhibition*, (Feb. 21, 2000), 1 page.

Koch, B. R., et al., "Antibacterial Activity of Structural analogs of Betulin Against *Escherichia coli, Bacillus subtilis*, and Methicillin–Resistant *Staphylococcus aureus*", *University of Minnesota Duluth, Sixteenth Annual Sigma XI–Duluth.*

*Scientific Poster Exhibition*, (Feb. 21, 2000), 1 page.

Nayar, V., et al., "Effectiveness of Triterpenoid Compounds and Polyethyleneimine Derivatives of Betulin Against Human Pathogenic Candida Species", *University of Minnesota Duluth, Sixteenth Annual Sigma XI–Duluth Scientific Poster Exhibition*, (Feb. 21, 2000), 1 page.

Verma, D. K., et al., "Antimicrobial Active Triterpenoids From Lantana Species", *Indian Drugs, vol. 34, No. 7, XP002115069*, (1997), pp. 390–392.

* cited by examiner

*Primary Examiner*—Kevin E. Weddington
(74) *Attorney, Agent, or Firm*—Schwegman, Lundberg, Woessner & Kluth, P.A.

(57) ABSTRACT

Methods of treating a bacterial infection and of killing or inhibiting bacteria are disclosed. The methods use derivatives of triterpenes that are abundant in birch bark and other plants. The triterpenes include betulin, allobetulin, and lupeol.

40 Claims, No Drawings

TRITERPENES HAVING ANTIBACTERIAL ACTIVITY

RELATED REFERENCES

This application claims priority from U.S. Provisional Application No. 60/236,510, filed on Sep. 29, 2000, which is incorporated by reference herein.

BACKGROUND OF THE INVENTION

Betulin is a pentacyclic triterpenoid derived from the outer bark of paper birch trees (*Betula paperifera*). It can be present at concentrations of up to about 24% of the bark of white birch. *Merck Index*, twelfth edition, page 1236, 1996. Lupeol is a related compound also found in birch bark and in other plant sources. Lupeol is present at concentrations of about 1.5–3% of birch bark and at up to about 8.2% in *Canavalia ensiformis*, a plant widespread in the humid tropics of Asia, India, and Africa. Allobetulin is another triterpenoid found in birch bark. A typical pulp mill that processes birch produces enough bark waste to allow for the inexpensive isolation of significant quantities of these triterpenoids.

Several triterpenoids have been found to have utility. For example, betulin and related compounds have been shown to have anti-viral activity against herpes simplex virus. Carlson et al., U.S. Pat. No. 5,750,578.

Bacteria are very common pathogens of humans. Among the bacterial species that cause serious disease are the gram negative bacterium *Escherichia coli* and gram positive bacteria of the genus Staphylococcus. *Staphylococcus aureus* is the most serious pathogen of the Staphylococcus bacteria, It is estimated to causes 13% of the 2 million hospital infections each year, and result in 80,000 deaths in the United States. Staphylococcal infections occur most commonly in persons weakened by poor health or immunodeficiency.

Antibiotic resistance of bacteria is a growing problem. New agents active against bacteria are needed. A need particularly exists for agents that will act against a range of species, including gram-negative and gram-positive species. Ideally, new agents would also be inexpensive to manufacture. New anti-bacterial agents would be less expensive to manufacture if they were abundant natural products or were easily synthesized from abundant natural products.

SUMMARY OF THE INVENTION

The present invention provides a therapeutic method of treating a mammal afflicted with a bacterial infection, the method comprising administering to the mammal an effective antibacterial amount of a triterpene of formula (I):

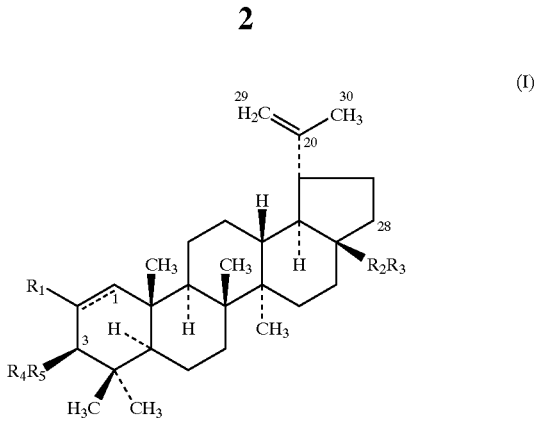

wherein $R_1$ is hydrogen or hydroxy;

$R_2$ is a direct bond, carbonyl, oxy, thio, carbonyl oxy, oxy carbonyl, $(C_6–C_{10})$aryl, or $(C_1–C_6)$alkyl;

$R_3$ is hydrogen, hydroxy, $(C_1–C_6)$alkyl, $O=P(OH)_2$, $O=P(OH)_2OP(O)(OH)—$, $(C_1–C_5)$alkanoyl, $Si(R)_3$ wherein each R is H, phenyl or $(C_1–C_6)$alkyl, $C(O)N(R)_2$, benzyl, benzoyl, tetrahydropyran-2-yl, 1-[$(C_1–C_4)$alkoxy]$(C_1–C_4)$alkyl, or a glycoside;

$R_4$ is hydrogen, hydroxy, $(C_1–C_6)$alkyl, $O=P(OH)_2$, $O=P(OH)_2$, $O=P(OH)_2OP(O)(OH)—$, $(C_1–C_5)$alkanoyl, $Si(R)_3$ wherein each R is H, phenyl or $(C_1–C_6)$alkyl, $C(O)N(R)_2$, benzyl, benzoyl, tetrahydropyran-2-yl, 1-[$(C_1–C_4)$alkoxy]$(C_1–C_4)$alkyl, a glycoside, or amino; or $R_4$ and $R_5$ together are oxo or (=NOH); and $R_5$ is direct bond, carbonyl, oxy, thio, carbonyl oxy, oxy carbonyl, $(C_6–C_{10})$aryl, or $(C_1–C_6)$alkyl; or $R_4$ and R, together are oxo or (=NOH);

wherein any alkyl can optionally be substituted with one or more halo, hydroxy, $(C_6–C_{10})$aryl, nitro, cyano, $(C_1–C_6)$alkoxy, trifluoromethyl, polyethyleneimine, poly(ethylene glycol), oxo, $NR_7R_8$, wherein $R_7$ and $R_8$ are each independently hydrogen, $(C_1–C_6)$alkyl or polyethyleneimine; $—OP(=O)(OH)_2$; or $C(=O)OR_9$, wherein $R_9$ is hydrogen, $(C_1–C_6)$alkyl, or polyethyleneimine;

each of the bonds represented by—is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, $(C_1–C_6)$alkoxy, trifluoromethyl, polyethyleneimine, poly(ethylene glycol), oxo, $NR_7R_8$, wherein $R_7$ and $R_8$ are each independently hydrogen, $(C_1–C_6)$alkyl or polyethyleneimine; or $C(=O)OR_9$, wherein $R_9$ is hydrogen, $(C_1–C_6)$alkyl, or polyethyleneimine;

or a pharmaceutically acceptable salt thereof.

The present invention also provides a therapeutic method of treating a mammal afflicted with a bacterial infection, the method comprising administering to the mammal an effective antibacterial amount of a triterpene of formula (II):

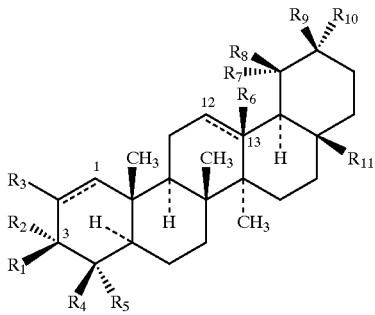

(II)

wherein

- one of $R_1$ and $R_2$ is —O—Y and the other is hydrogen or $(C_1-C_6)$alkyl optionally substituted by hydroxy, $(C_1-C_6)$alkoxy, halo, halo$(C_1-C_6)$alkoxy or $NR_jR_k$ wherein $R_j$ and $R_k$ are independently H, $(C_1-C_6)$alkyl or $(C_1-C_6)$alkanoyl; or $R_1$ and $R_2$ together are oxo (=O);
- $R_3$ is hydrogen, halo, carboxy, mercapto, $(C_1-C_6)$alkyl, $(C_3-C_8)$cycloalkyl, or —o—Y;
- $R_4$ and $R_5$ are each independently hydrogen, $(C_1-C_6)$alkyl, or hydroxy$(C_1-C_6)$alkyl;
- $R_6$ is hydrogen or is absent when the adjacent—is a bond;
- $R_7$ is hydrogen or $(C_1-C_6)$alkyl;
- $R_8$ is hydrogen, $(C_1-C_6)$alkyl, or hydroxy$(C_1-C_6)$alkyl and $R_{11}$ is hydrogen, $(C_1-C_6)$alkyl carboxy, or hydroxy $(C_1-C_6)$alkyl; or $R_8$ and $R_{11}$ together are —O—C(=X)—;
- $R_9$ and $R_{10}$, are each independently hydrogen or $(C_1-C_6)$alkyl;
- each of the bonds represented by—is independently absent or is present;
- X is two hydrogens, oxo (=O) or thioxo (=S);
- each Y is independently H, aryl, $P(O)(Cl)_2$, $(C_3-C_8)$cycloalkyl, adamantyl, —$SO_2R_a$ O=$P(R_b)_2$, O=$P(R_c)_2OP(O)(R_d)$—, $Si(R_e)_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N(Rf)—; wherein said chain may optionally be substituted on carbon with 1, 2, 3, or 4 oxo (=O), hydroxy, carboxy, halo, mercapto, nitro, —$N(R_g)(R_h)$, $(C_3-C_8)$cycloalkyl, $(C_3-C_8)$cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated (e.g. containing one, two, three or more, double or triple bonds);
- $R_a$ is $(C_1-C_6)$alkyl or aryl;
- $R_b$, $R_c$, and $R_d$ are each independently hydroxy, $(C_1-C_6)$alkoxy, hydroxy$(C_2-C_6)$alkoxy, adamantyloxy, adamantyl$(C_1-C_6)$alkoxy, norbornyloxy, 1,1-di(hydroxymethyl)-2-hydroxyethoxy, carboxy$(C_1-C_6)$alkoxy, 2,3-epoxypropyloxy, benzyloxy, $(C_3-C_8)$cycloalkyloxy, $NR_xR_y$, or aryloxy;
- $R_e$ is H, aryl or $(C_1-C_6)$alkyl;
- $R_f$ is hydrogen, $(C_1-C_6)$alkyl, $(C_1-C_6)$alkanoyl, phenyl or benzyl;
- $R_g$ and $R_h$ are each independently selected from the group consisting of hydrogen, $(C_1-C_6)$alkyl, hydroxy$(C_1-C_6)$alkyl, adamantyl, adamantyl$(C_1-C_6)$alkyl, amino$(C_1-C_6)$alkyl, aminosulfonyl, $(C_1-C_6)$alkanoyl, aryl and benzyl; or $R_b$ and $R_c$ together with the nitrogen to which they are attached form a pyrrolidino, piperidino, or morpholino radical; and
- $R_x$ and $R_y$ are each independently hydrogen, $(C_1-C_6)$alkyl, $(C_1-C_6)$alkanoyl, aryl or benzyl;

wherein each aryl of Y, $R_a$—$R_d$, $R_g$—$R_h$, $R_x$, and $R_y$ may optionally be substituted by 1, 2, or 3 aminosulfonyl, carboxy, $NR_iR_j$, $(C_1-C_6)$alkyl, $(C_1-C_6)$alkoxy, hydroxy, halo, nitro, cyano, mercapto, carboxy, hydroxy$(C_1-C_6)$alkyl, halo$(C_1-C_6)$alkyl, trifluoromethoxy, $(C_1-C_6)$alkanoyl, $(C_1-C_6)$alkoxycarbonyl, $(C_1-C_6)$alkylthio, or $(C_1-C_6)$alkanoyloxy; wherein $R_i$ and $R_j$ are each independently hydrogen, $(C_1-C_6)$alkyl, $(C_1-C_6)$alkanoyl, phenyl, or benzyl;

wherein any alkyl can optionally be substituted with one or more polyethyleneimine or poly(ethylene glycol); and wherein any alkyl can optionally be interrupted with one or more polyethyleneimine or poly(ethylene glycol);

or a pharmaceutically acceptable salt thereof.

The present invention also provides a method of inhibiting or killing a bacterium, the method comprising contacting the bacterium with an effective antibacterial amount of a triterpene of formula (I):

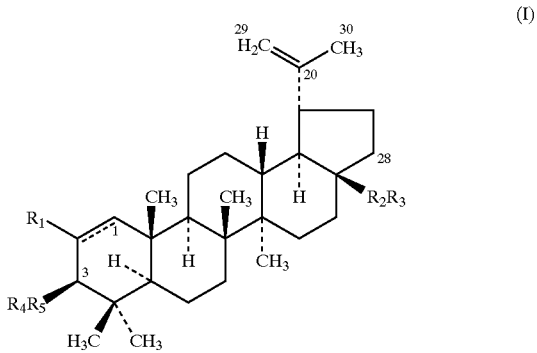

(I)

wherein

- $R_1$ is hydrogen or hydroxy;
- $R_2$ is a direct bond, carbonyl, oxy, thio, carbonyl oxy, oxy carbonyl, $(C_6-C_{10})$aryl, or $(C_1-C_6)$alkyl;
- $R_3$ is hydrogen, hydroxy, $(C_1-C_6)$alkyl, O=$P(OH)_2$, O=$P(OH)_2OP(O)(OH)$—, $(C_1-C_5)$alkanoyl, $Si(R)_3$ wherein each R is H, phenyl or $(C_1-C_6)$alkyl, $C(O)N(R)_2$, benzyl, benzoyl, tetrahydropyran-2-yl, 1-[$(C_1-C_4)$alkoxy]$(C_1-C_4)$alkyl, or a glycoside;
- $R_4$ is hydrogen, hydroxy, $(C_1-C_6)$alkyl, O=$P(OH)_2$, O=$P(OH)_2OP(O)(OH)$—, $(C_1-C_5)$alkanoyl, $Si(R)_3$ wherein each R is H, phenyl or $(C_1-C_6)$alkyl, $C(O)N(R)_2$, benzyl, benzoyl, tetrahydropyran-2-yl, 1-[$(C_1-C_4)$alkoxy]$(C_1-C_4)$alkyl, a glycoside, or amino; or $R_4$ and $R_5$ together are oxo or (=NOH); and $R_5$ is direct bond, carbonyl, oxy, thio, carbonyl oxy, oxy carbonyl, $(C_6–C_{10})$aryl, or $(C_1–C_6)$alkyl; or $R_4$ and $R_5$ together are oxo or (=NOH);

wherein any alkyl can optionally be substituted with one or more halo, hydroxy, $(C_6–C_{10})$aryl, nitro, cyano, $(C_1–C_6)$alkoxy, trifluoromethyl, polyethyleneimine, poly(ethylene glycol), oxo, $NR_7R_8$, wherein $R_7$ and $R_8$ are each independently hydrogen, $(C_1–C_6)$alkyl or polyethyleneimine; —OP(=O)(OH)$_2$; or C(=O)OR$_9$, wherein $R_9$ is hydrogen, $(C_1–C_6)$alkyl, or polyethyleneimine;

each of the bonds represented by — is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, $(C_1–C_6)$alkoxy, trifluoromethyl, polyethyleneimine, poly(ethylene glycol), oxo, $NR_7R_8$, wherein $R_7$ and $R_8$ are each independently hydrogen, $(C_1–C_6)$alkyl or polyethyleneimine; or C(=O)OR$_9$, wherein $R_9$ is hydrogen, $(C_1–C_6)$alkyl, or polyethyleneimine;

or a pharmaceutically acceptable salt thereof.

The present invention also provides a method of inhibiting or killing a bacterium, the method comprising contacting the bacterium with an effective antibacterial amount of a triterpene of formula (II):

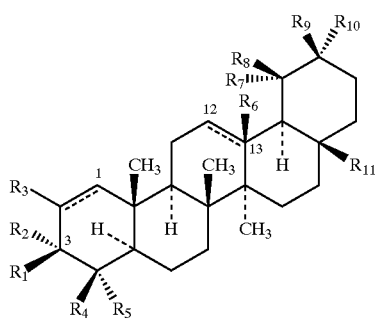

(II)

wherein
one of $R_1$ and $R_2$ is —O—Y and the other is hydrogen or $(C_1–C_6)$alkyl optionally substituted by hydroxy, $(C_1–C_6)$alkoxy, halo, halo$(C_1–C_6)$alkoxy or $NR_jR_k$ wherein $R_j$ and $R_k$ are independently H, $(C_1–C_6)$alkyl or $(C_1–C_6)$alkanoyl; or $R_1$ and $R_2$ together are oxo (=O);

$R_3$ is hydrogen, halo, carboxy, mercapto, $(C_1–C_6)$alkyl, $(C_3–C_8)$cycloalkyl, or —O—Y;

$R_4$ and $R_5$ are each independently hydrogen, $(C_1–C_6)$alkyl, or hydroxy$(C_1–C_6)$alkyl;

$R_6$ is hydrogen or is absent when the adjacent — is a bond;

$R_7$ is hydrogen or $(C_1–C_6)$alkyl;

$R_8$ is hydrogen, $(C_1–C_6)$alkyl or hydroxy$(C_1–C_6)$alkyl and $R_{11}$ is hydrogen, $(C_1–C_6)$alkyl, carboxy, or hydroxy$(C_1–C_6)$alkyl; or $R_8$ and $R_{11}$ together are —O—C(=X)—;

$R_9$ and $R_{10}$, are each independently hydrogen or $(C_1–C_6)$alkyl;

each of the bonds represented by — is independently absent or is present;

X is two hydrogens, oxo (=O) or thioxo (=S);

each Y is independently H, aryl, P(O)(Cl)$_2$, $(C_3–C_8)$cycloalkyl, adamantyl, —SO$_2$R$_a$, O=P(R$_b$)$_2$, O=P(R$_c$)$_2$OP(O)(R$_d$)—, Si(R$_e$)$_3$, tetrahydropyran-2-yl, an amino acid, a peptide, a glycoside, or a 1 to 10 membered branched or unbranched carbon chain optionally comprising 1, 2, or 3 heteroatoms selected from non-peroxide oxy, thio, and —N(R$_f$)—; wherein said chain may optionally be substituted on carbon with 1, 2, 3, or 4 oxo (=O), hydroxy, carboxy, halo, mercapto, nitro, —N(R$_g$)(R$_h$), $(C_3–C_8)$cycloalkyl, $(C_3–C_8)$cycloalkyloxy, aryl, aryloxy, adamantyl, adamantyloxy, hydroxyamino, trifluoroacetylamino, a glycoside, an amino acid, or a peptide; and wherein said chain may optionally be saturated or unsaturated (e.g. containing one, two, three or more, double or triple bonds);

$R_a$ is $(C_1–C_6)$alkyl or aryl;

$R_b$, $R_c$, and $R_d$ are each independently hydroxy, $(C_1–C_6)$alkoxy, hydroxy$(C_2–C_6)$alkoxy, adamantyloxy, adamantyl$(C_1–C_6)$alkoxy, norbornyloxy, 1,1-di(hydroxymethyl)-2-hydroxyethoxy, carboxy$(C_1–C_6)$alkoxy, 2,3-epoxypropyloxy, benzyloxy, $(C_3–C_8)$cycloalkyloxy, $NR_xR_y$, or aryloxy;

$R_e$ is H, aryl or $(C_1–C_6)$alkyl;

$R_f$ is hydrogen, $(C_1–C_6)$alkyl, $(C_1–C_6)$alkanoyl, phenyl or benzyl;

$R_g$ and $R_h$ are each independently selected from the group consisting of hydrogen, $(C_1–C_6)$alkyl, hydroxy$(C_1–C_6)$alkyl, adamantyl, adamantyl$(C_1–C_6)$alkyl, amino$(C_1–C_6)$alkyl, aminosulfonyl, $(C_1–C_6)$alkanoyl, aryl and benzyl; or $R_b$ and $R_c$ together with the nitrogen to which they are attached form a pyrrolidino, piperidino, or morpholino radical; and $R_x$ and $R_y$ are each independently hydrogen, $(C_1–C_6)$alkyl, $(C_1–C_6)$alkanoyl, aryl or benzyl;

wherein each aryl of Y, $R_a$—$R_d$, $R_g$—$R_h$, $R_x$, and $R_y$ may optionally be substituted by 1, 2, or 3 aminosulfonyl, carboxy, $NR_iR_j$, $(C_1–C_6)$alkyl, $(C_1–C_6)$alkoxy, hydroxy, halo, nitro, cyano, mercapto, carboxy, hydroxy$(C_1–C_6)$alkyl, halo$(C_1–C_6)$alkyl, trifluoromethoxy, $(C_1–C_6)$alkanoyl, $(C_1–C_6)$alkoxycarbonyl, $(C_1–C_6)$alkylthio, or $(C_1–C_6)$alkanoyloxy; wherein $R_i$ and $R_j$ are each independently hydrogen, $(C_1–C_6)$alkyl, $(C_1–C_6)$alkanoyl, phenyl, or benzyl;

wherein any alkyl can optionally be substituted with one or more polyethyleneimine or poly(ethylene glycol); and wherein any alkyl can optionally be interrupted with one or more polyethyleneimine or poly(ethylene glycol);

or a pharmaceutically acceptable salt thereof.

The present invention provides a therapeutic method of treating a mammal afflicted with a bacterial infection, the method comprising administering to the mammal an effective antibacterial amount of a triterpene of formula (I):

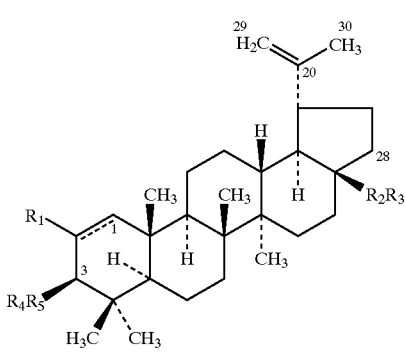

(I)

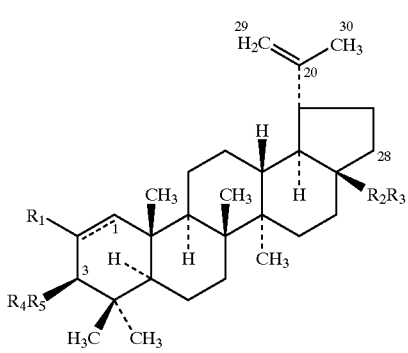

(I)

wherein

R$_1$ is hydrogen or hydroxy;

R$_2$ is a direct bond, carbonyl, oxy, thio, carbonyl oxy, oxy carbonyl, (C$_6$–C$_{10}$)aryl, or (C$_1$–C$_6$)alkyl;

R$_3$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, or a glycoside;

R$_4$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, or a glycoside; or R$_4$ and R$_5$ together are oxo; and R$_5$ is direct bond, carbonyl, oxy, thio, carbonyl oxy, oxy carbonyl, (C$_6$–C$_{10}$)aryl, or (C$_1$–C$_6$)alkyl; or R$_4$ and R$_5$ together are oxo;

wherein any alkyl can optionally be substituted with one or more halo, hydroxy, (C$_6$–C$_{10}$)aryl, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; —OP(=O)(OH)$_2$; or C(=O)OR$_9$, wherein R$_9$ is hydrogen, (C$_1$–C$_6$)alkyl, or polyethyleneimine;

each of the bonds represented by—is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; or C(=O)OR$_9$, wherein R$_9$ is hydrogen, (C$_1$–C$_6$)alkyl, or polyethyleneimine;

or a pharmaceutically acceptable salt thereof.

The present invention also provides a method of inhibiting or killing a bacterium, the method comprising contacting the bacterium with an effective antibacterial amount of a triterpene of formula (I):

wherein

R$_1$ is hydrogen or hydroxy;

R$_2$ is a direct bond, carbonyl, oxy, thio, carbonyl oxy, oxy carbonyl, (C$_6$–C$_{10}$)aryl, or (C$_1$–C$_6$)alkyl;

R$_3$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, or a glycoside;

R$_4$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, or a glycoside; or R$_4$ and R$_5$ together are oxo; and R$_5$ is direct bond, carbonyl, oxy, thio, carbonyl oxy, oxy carbonyl, (C$_6$–C$_{10}$)aryl, or (C$_1$–C$_6$)alkyl; or R$_4$ and R$_5$ together are oxo;

wherein any alkyl can optionally be substituted with one or more halo, hydroxy, (C$_6$–C$_{10}$)aryl, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; —OP(=O)(OH)$_2$; or C(=O)OR$_9$, wherein R$_9$ is hydrogen, (C$_1$–C$_6$)alkyl, or polyethyleneimine;

each of the bonds represented by—is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; or C(=O)OR$_9$, wherein R$_9$ is hydrogen, (C$_1$–C$_6$)alkyl, or polyethyleneimine;

or a pharmaceutically acceptable salt thereof.

The invention provides novel compounds of formula (I) and formula (II), intermediates for the synthesis of compounds of formula (I) and formula (II), as well as methods of preparing compounds of formula (I) and (II). The invention also provides compounds of formula (I) and (II) that are useful as intermediates for the synthesis of other useful compounds. The invention provides for the use of compounds of formula (I) and formula (II) for the manufacture of medicaments useful for the treatment of bacterial infections in a mammal, such as a human.

DETAILED DESCRIPTION

The following definitions are used, unless otherwise described: halo is fluoro, chloro, bromo, or iodo. Alkyl, alkoxy, alkenyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

It will be appreciated by those skilled in the art that compounds useful in the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound useful in the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antibacterial activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; partially unsaturated $(C_2-C_6)$alkyl or $(C_2-C_6)$alkenyl can be vinyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_1-C_5)$alkanoyl can be carbonyl, acetyl, propanoyl, butanoyl, isopropanoyl, or pentenoyl; $(C_1-C_6)$alkoxy can be methoxy, ethoxy, propoxy, isopropoxy, butoxy, iso-butoxy, sec-butoxy, pentoxy, 2-pentoxy, 3-pentoxy, or hexyloxy; halo$(C_1-C_6)$alkoxy can be trifluoromethyloxy, 2-chloroethyloxy, 3,3-dichloropropyloxy, or 4,4,4-trifluorobutyloxy; $(C_3-C_8)$cycloalkyl can be cyclopropyl, cyclobutyl, cyclopentyl, cyclohexyl, cycloheptyl, or cyclooctyl; $(C_3-C_8)$cycloalkyloxy can be cyclopropyloxy, cyclobutyloxy, cyclopentyloxy, cyclohexyloxy, cycloheptyloxy, or cyclooctyloxy; hydroxy$(C_1-C_6)$alkoxy can be hydroxymethoxy, 1-hydroxyethoxy, 2-hydroxyethoxy, 1-hydroxypropoxy, 2-hydroxypropoxy, 3-hydroxypropoxy, 1-hydroxybutoxy, 4-hydroxybutoxy, 1-hydroxypentoxy, 5-hydroxypentoxy, 1-hydroxyhexoxy, or 6-hydroxyhexoxy; amino$(C_1-C_6)$alkyl can be aminomethyl, 1-aminoethyl, 2-aminoethyl, 1-aminopropyl, 2-aminopropyl, 3-aminopropyl, 1-aminobutyl, 2-aminobutyl, 3-aminobutyl, 4-aminobutyl, 1-aminopentyl, 2-aminopentyl, 3-aminopentyl, 5-aminopentyl, 1-aminohexyl, 2-aminohexyl, 3-aminohexyl, or 6-aminohexyl; $(C_1-C_6)$alkoxycarbonyl can be methoxycarbonyl, ethoxycarbonyl, propyloxycarbonyl, isopropyloxycarbonyl, 2-methylpropyloxycarbonyl, butyloxycarbonyl, pentyloxycarbonyl, or hexyloxycarbonyl; $(C_1-C_6)$alkanoyloxy can be carbonyloxy, acetyloxy, propanoyloxy, butanoyloxy, 2-methylpropanoyloxy, 2-methylbutanoyloxy, 3-methylbutanoyloxy, pentanoyloxy, or hexanoyloxy.

"3-carboxypropenoyloxymethyl" refers to the group —CH$_2$OC(=O)CH=CHCOOH;

"aminoacetoxymethyl" refers to the group —CH$_2$OC(=O)CH$_2$NH$_2$;

"(carboxymethoxy)acetoxymethyl" refers to the group —CH$_2$OC(=O)CH$_2$OCH$_2$COOH;

"4-carboxybutanoyloxymnethyl" refers to the group —CH$_2$OC(=O)CH$_2$CH$_2$CH$_2$COOH;

"2-carboxybenzoyloxymethyl" refers to the group

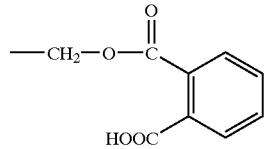

"butanoyloxymethyl" refers to the group —CH$_2$OC(=O)CH$_2$CH$_2$CH$_3$;

"2-carboxybenzoyl" refers to the group

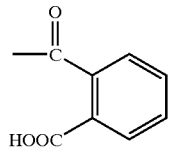

"2-amino-3-methylbutanoyl" refers to the group —C(=O)CH$_2$(NH$_2$)CH$_2$(CH$_3$)$_2$;

"3-carboxypropenoyl" refers to the group -C(=O)CH=CHCOOH;

"aminoacetyl" refers to the group —C(=O)CH$_2$NH$_2$;

"4-carboxybutanoyl" refers to the group —C(=O)CH$_2$CH$_2$CH$_3$COOH,

"(carboxymethoxy)acetyl" refers to the group —C(=O)CH$_2$OCH$_2$COOH,

"3-(3,4-dihydroxyphenyl)propenoyl" refers to the group

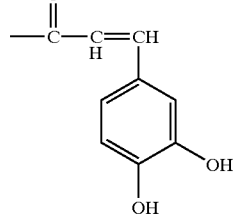

"carboxymethylenethioacetyl" refers to the group —C(=O)CH$_2$SCH$_2$COOH;

"3-carboxy-3-methylbutanoyl" refers to the group —C(=O)CH$_2$C(COOH)(CH$_3$)$_2$;

"oxime" refers to the group (=NOH) that is substituted directly on a carbon atom, thereby providing the group C=N—OH.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$–$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, Third Edition, 1999, and references cited therein). An amino acid can be linked to the remainder of a compound of formula I or II through the carboxy terminus, the amino terminus, or through any other convenient point of attachment, such as, for example, through the sulfur of cysteine.

The term "peptide" describes a sequence of 2 to 25 amino acids (e.g. as defined herein) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I or II through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620.

Glycosides are formed by reacting mono-, di- and polysaccharides with 1–2 hydroxyl groups of the compound of formula (I) or formula (II), including glucose, glucuronic acid, mannose, galactose, sorbase, ribose, maltose, sucrose, modified cellulosics, dextrans, modified starches and the like. These derivatives can advantageously exhibit improved water solubility over betulin itself. See, *Remington's Pharmaceutical Sciences*, A. R. Gennaro, ed., Mack Pub. Co. (18th ed., 1990) at pages 384–386. Glycoside derivatives can be prepared as described in PCT Applications WO 96/34005 and 97/03995.

"Polyethyleneimine" refers to the group (—$NHCH_2CH_2$—)$_x$[—$N(CH_2CH_2NH_2)CH_2CH_2$—]$_y$. Polyethyleneimine can be attached to a compound of formula I or II through either of the nitrogen atoms marked with hash marks. "Poly(ethylene glycol)" refers to the compound H($OCH_2CH_2$)$_n$OH. It can be attached to a compound of formula I or II through the terminal hydroxyl group.

The term "partially unsaturated" refers to a linear or branched hydrocarbon having one or more carbon—carbon double bonds.

The term "phosphono" refers to O=P(OH)$_2$—.

The term "direct bond" refers to a group being absent.

Combinations of substituents and/or variables are permissible only if such combinations result in stable compounds. By "stable compound" is meant herein a compound that is sufficiently robust to survive isolation to a useful degree of purity from a reaction mixture, and formulation into an efficacious antibacterial agent.

The term "bacterium" or "bacteria" refers to any prokaryotic organism.

The structure and carbon numbering of three exemplary compounds of the present invention are shown below.

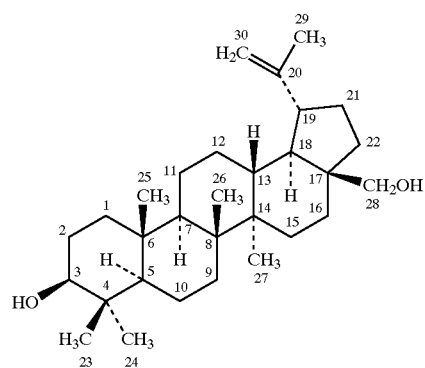

Betulin

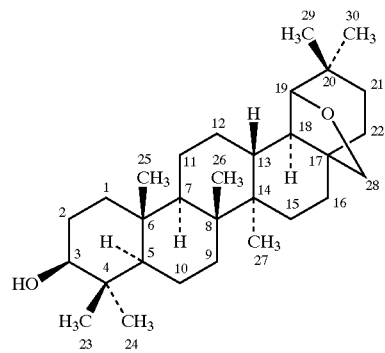

Allobetulin

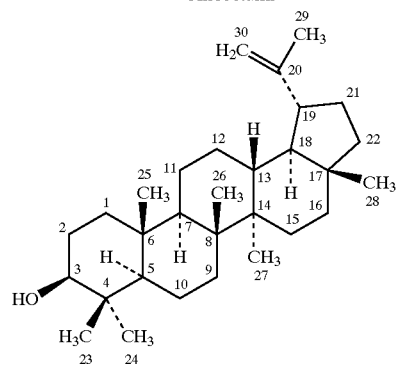

Lupeol

Specific values for compounds of formula (I) are as follows:

A specific value for the bond between carbons 1 and 2 is a single bond.

Another specific value for the bond between carbons 1 and 2 is a double bond.

A specific value for $R_1$ is hydrogen.

Another specific value for $R_1$ is hydroxy.

A specific value for $R_2$ is a direct bond.

A specific value for $R_3$ is($C_1$–$C_6$)alkyl; wherein any alkyl can optionally be substituted with one or more oxo, carboxy, amino, ($C_6$–$C_{10}$)aryl, or —OP(=O)(OH)$_2$; any alkyl is optionally interrupted on carbon with one or more oxy or thio; any alkyl is optionally partially unsaturated; and any aryl can optionally be substituted with one or more hydroxy or carboxy.

Another specific value for $R_3$ is 3-carboxypropenoyloxymethyl, aminoacetoxymethyl, (carboxymethoxy)acetoxymethyl, 4-carboxybutanoyloxymethyl, 2-carboxybenzoyloxymethyl, butanoyloxymethyl, or —$CH_2OC$(=O)OP(=O)(OH)$_2$.

A specific value for $R_4$ is $(C_1-C_6)$alkyl; wherein any alkyl can optionally be substituted with one or more oxo, carboxy, amino, $(C_6-C_{10})$aryl, or $-OP(=O)(OH)_2$; any alkyl is optionally interrupted on carbon with one or more oxy or thio; any alkyl is optionally partially unsaturated; and any aryl can optionally be substituted with one or more hydroxy or carboxy.

Another specific value for $R_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, $-P(=O)(OH)_2$, oxo, or $(=NOH)$.

A specific value for $R_5$ is oxy or a direct bond.

A specific group of compounds are compounds of formula (I) wherein $R_1$ is hydrogen or hydroxy; $R_2$ is a direct bond; $R_3$ is $(C_1-C_5)$alkoxymethyl or hydroxymethyl; $R_4$ is hydrogen, phosphono, sulfo, or $(C_1-C_6)$alkyl, and $R_5$ is oxy; or $R_4$ is amino and $R_5$ is a direct bond; or $R_4$ and $R_5$ together are oxo or $(=NOH)$; wherein any alkyl, or alkyl segment of an R group, is optionally interrupted on carbon with one or more oxy, thio, or imido; wherein any alkyl, or alkyl segment of an R group, can optionally be substituted with one or more oxo, carboxy, amino, $-OP(=O)(OH)_2$, or phenyl; wherein phenyl can optionally be substituted with one or more hydroxy or carboxy.

Another specific group of compounds are compounds of formula (I) wherein $R_1$ is hydrogen or hydroxy; $R_2$ is a direct bond; $R_3$ is 3-carboxypropenoyloxymethyl, aminoacetoxymethyl, (carboxmethoxy)acetoxymethyl, 4-carboxybutanoyloxymethyl, 2-carboxybenzoyloxymethyl, butanoyloxymethyl, or $-CH_2OC(=O)OP(=O)(OH)_2$; $R_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, $-P(=O)(OH)_2$, oxo, or $(=NOH)$; and $R_5$ is oxy or a direct bond.

Another specific group of compounds of formula (I) is betulin; betulin-3,28-diglycine; betulin-28-glycerol oxalate; betulin-28-glycine; betulin-28-oxalate; betulin arabinose galactan; betulin-3,28-didiglycolate; betulin-3,28-diglycine; betulin-3-maleate; betulin-3,28-di-(L-Glutamic acid r-benzylester) ester; betulin-3,28-di-L-alanine; betulin-3,28-di-L-proline; betulin-3,28-dioxalate; betulin-1-ene-2-ol; betulin-3,28-diphenylalanine; betulin-3-28-dioxalate-polyethylene amine; betulin-3,38-diphosphate; betulin-3-caffeate; betulin-3,28-(3',3'-dimethyl) glutarate; betulin-28-diglycolate; betulin-28-glutarate; betulin-28-maleate; betulin-28-phthalate; betulin-3,28-di(3',3'-dimethyl) glutarate; betulin-3,28-didiglycolate; betulin-3,28-di(thiodiglycolate); betulin-3,28-diglutarate; betulin-3,28-dimaleate; betulin-3,28-diglycolate; betulin-3,28-diphthalate; betulin-3,28-di-L-phenylalanine; betulin-3,28-di-L-valine; betulin-28-succinate; betulin-3,28-disuccinate; betulin-3,28-di-(polyethylene glycol)-COOH (Mw=1448); betulin-3,28-di-(polyethylene glycol)-COOH (Mw=906 crude); betulin-3,28-di-(polyethylene glycol)-COOH (Mw=906 pure); betulinic acid; betulon-1-ene-2-ol; betulin-3,28-(dipoly(ethylene glycol)bis (carboxymethylester); allobetulin-3,28-(dipoly(ethylene glycol)bis (carboxymethyl ester); hederin hydrate; lupeol; lupeol-3-glutarate; lupeol-3-succinate; lupeol-3-thiodiglycolate; lupeol-3-phthalate; lupeol-3-succinate; oleanolic acid; ursolic acid; or uvaol.

Another specific group of compounds of formula (I) is betulin; betulin-28-glycerol oxalate; betulin-28-oxalate; betulin arabinose galactan; betulin-3,28-didiglycolate; betulin-3,28-diglycine; betulin-3,28-di-(L-glutamic acid y-benzylester) ester; betulin3,28-di-L-proline ester; betulin-3,28-dioxalate; betulin-1-ene-2-ol; betulin-3,28-dioxalate-polyethylene amine; betulin-3,28-diphosphate; betulin-3-caffeate; betulin-28-diglycolate; betulin-28-glutarate; betulin-28-maleate; betulin-28-phthalate; betulin-3,28-dithiodiglycolate; betulin-3,28-diglutarate; betulin-3,28-dimaleate; betulin-3,28-diglycolate; betulin-3,28-diphthalate; betulin-3,28-di-L-phenylalanine; betulin-di-L-valine; betulin-28-succinate; betulin-3,28-disuccinate; betulin-3,28-di-(polyethylene glycol)-COOH (Mw=906 pure); betulinic acid; betulon-1-ene-2-ol; betulin-3,28-(dipoly(ethylene glycol)bis (carboxymethylester); hederin hydrate; lupeol-3-glutarate; lupeol-3-succinate; lupeol-3-thiodiglycolate; lupeol-3-phthalate; oleanolic acid; or uvaol.

Another specific group of compounds of formula (I) is betulin-3-caffeate; betulin-28-diglycolate; betulin-3,28-diglutarate; betulin-3,28-diglycine; betulin-3,28-didiglycolate; betulin-3,28-dimaleate; betulin-3,28-diphosphate; betulin-3,28-diphthalate; betulin-3,28-di-L-valine; lupeol; lupeol-3-amine; lupeol-3-(3',3'-dimethyl) succinate; lupeol-3-maleate; lupeol-3-phosphate; lupeol-3-thiodiglycolate; lupenone; lupenon-1,2-ene-2-ol; or lupenon-3-oxime.

A specific group of compounds of formula (II) is 3-β-acetoxy-19αH-19,28 lactone oleanan; allobetulin; allobetulin-3-succinate; allobetulin-3-glycine ester; allobetulin lactone; allobetulin lactone-3-acetate; allobetulin lactone-3-phosphate; allobetulin-3-L-alanine; allobetulin-3-L-valine; allobetulin-3-L-proline; allobetulin-3-succinate; allobetulin-3-diglycolate; allobetulin-3-glutarate; allobetulin-3-phthalate; allobetulin-3-methylenamine; allobetulin-3-ethanolamine; allobetulin-3-ethanolamine hydrochloride; allobetulin-3-glycolate; allobetulin-3-glutarate; allobetulin-28-glutarate; allobetulin-3-methylamine HCl; allobetulin-3-phosphate; allobetulin-3-(polyethylene glycol)-COOH (Mw=674); allobetulon; allobetulon lactone-1-ene-2-ol; allobetulon lactone-1-en-2-succinate; allobetulon-1-ene-2-ol; allobetulon-1-ene-2-diglycolate; 3-allobetulon-1-ene-2-succinate; or 3-allobetulon-1-ene-2-diglycolate.

Another specific group of compounds of formula (II) are 3-β-acetoxy-19αH-19,28 lactone oleanan; allobetulin; allobetulin-3-glycine ester; allobetulin lactone-3-phosphate; allobetulin-3-succinate; allobetulin-3-ethanolamine; allobetulin-3-glutarate; allobetulin-28-glutarate; allobetulin-3-methylamine HCl; allobetulin-3-phosphate; allobetulon; allobetulon lactone-1-ene-2-ol; 3-allobetulon-1-ene-2-succinate; or ursolic acid.

A specific method of the invention is the method of treating a mammal afflicted with a bacterial infection comprising administering to the mammal an effective antibacterial amount of a compound of formula (I) or formula (II), wherein the bacterial infection is caused by *Escherichia coli*, Staphylococcus sp., *Enterococcus faecalis*, or a combination thereof.

Another specific method of the invention is the method of treating a mammal afflicted with a bacterial infection comprising administering to the mammal an effective antibacterial amount of a compound of formula (I) or formula (II), wherein the bacterial infection is caused by *Staphylococcus aureus*.

Another specific method of the invention is the method of inhibiting or killing a bacterium or bacteria comprising contacting the bacterium with an effective antibacterial amount of a triterpene of formula (I) or formula (II), wherein the bacterium is *Escherichia coli*, Staphylococcus sp., *Enterococcus faecalis*, or a combination thereof.

Another specific method of the invention is the method of inhibiting or killing a bacterium or bacteria comprising contacting the bacterium with an effective antibacterial amount of a triterpene of formula (I) or formula (II) wherein the bacterium is *Staphylococcus aureus*.

Another specific method of the invention is the method of inhibiting or killing a bacterium or bacteria comprising contacting the bacterium with an effective antibacterial amount of a triterpene of formula (I) wherein the contacting is in vivo.

Another specific method of the invention is the method of inhibiting or killing a bacterium or bacteria comprising contacting the bacterium with an effective antibacterial amount of a triterpene of formula (I) wherein the contacting is in vitro.

Another specific method of the invention is the method of inhibiting or killing a bacterium or bacteria comprising contacting the bacterium with an effective antibacterial amount of a triterpene of formula (II) wherein the contacting is in vivo.

Another specific method of the invention is the method of inhibiting or killing a bacterium or bacteria comprising contacting the bacterium with an effective antibacterial amount of a triterpene of formula (II) wherein the contacting is in vitro.

Specific triterpenes of formula (I) having antibacterial activity are shown below in Table 1 below.

TABLE 1

Specific compounds of formula (I) having anti-bacterial activity.

| Name | $R_1$ | $R_2$ | $R_3$ | $R_5$ | $R_4$ | Active against |
|---|---|---|---|---|---|---|
| Betulin-3-caffeate | H | — | 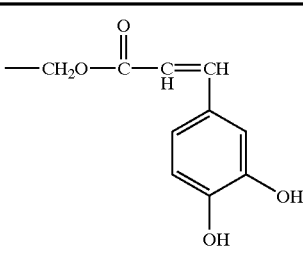 | —O— | 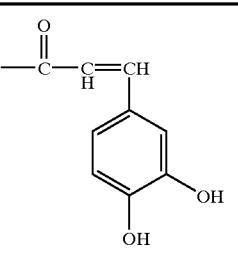 | *E. coli* |
| Betulin-28-diglycolate | H | — | —CH$_2$OC(=O)CH$_2$OCH$_2$COOH | —O— | H | *E. coli* |
| Betulin-3,28-diglutarate | H | — | —CH$_2$OC(=O)CH$_2$CH$_2$CH$_2$COOH | —O— | —C(=O)CH$_2$CH$_2$CH$_2$COOH | *E. coli* |
| Betulin-3,28-diglycine | H | — | —CH$_2$OC(=O)CH$_2$NH$_2$ | —O— | —C(=O)CH$_2$NH$_2$ | *E. coli* |
| Betulin-3,28-didiglycolate | H | — | —CH$_2$OC(=O)CH$_2$OCH$_2$COOH | —O— | —C(=O)CH$_2$OCH$_2$COOH | *E. coli* |
| Betulin-3,28-dimaleate | H | — | —CH$_2$OC(=O)CH=CHCOOH | —O— | —C(=O)CH=CHCOOH | *S. aureus*, *S. aureus* methicillin resistant |
| Betulin-3,28-diphosphate | H | — | —CH$_2$O—P(=O)(OH)$_2$ | —O— | —P(=O)(OH)$_2$ | *E. coli* |
| Betulin-3,28-diphthalate | H | — | 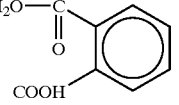 | —O— | 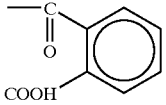 | *S. aureus* |
| Betulin-3,28-di-L-valine | H | — | —CH$_2$OC(=O)—CH$_2$(NH$_2$)CH(CH$_3$)$_2$ | —O— | —C(=O)—CH$_2$(NH$_2$)CH(CH$_3$)$_2$ | *S. aureus* |
| Lupeol | H | — | —CH$_3$ | —O— | H | *S. aureus*, *S. epidermidis*, *Enterococcus faecalis* |
| Lupeol-3-amine | H | — | —CH$_3$ | — | H | *S. aureus*, *E. faecalis* |
| Lupeol-3-(3',3',dimethyl)succinate | H | — | —CH$_3$ | —O— | —CH$_2$OC(=O)CH$_2$C(CH$_3$)$_2$COOH | *S. aureus* |
| Lupeol-3-phosphate | H | — | —CH$_3$ | —O— | —P(=O)(OH)$_2$ | *S. aureus*, *E. faecalis* |
| Lupeol-3-thiodiglycolate | H | — | —CH$_3$ | —O— | —C(=O)CH$_2$SCH$_2$COOH | *S. aureus*, *S. epidermidis*, *E. faecalis* |
| Lupeol-3-maleate | H | — | —CH$_3$ | —O— | —C(=O)CH=CHCOOH | *S. aureus*, *S. epidermidis*, *E. faecalis* |
| Lupenone | H | — | —CH$_3$ | — | (=O) | *S. aureus*, *E. faecalis* |

TABLE 1-continued

Specific compounds of formula (I) having anti-bacterial activity.

| Name | $R_1$ | $R_2$ | $R_3$ | $R_5$ | $R_4$ | Active against |
|---|---|---|---|---|---|---|
| Lupenon-3-oxime | H | — | —$CH_3$ | — | (=NOH) | S. aureus, E. faecalis |
| Lupenon-1,2-ene-2-ol | H | — | —$CH_3$ | — | (=O) | S. aureus, S. epidermidis, E. faecalis |

In addition, lupenon-1,2-ene-2-ol has a double bond between carbons 1 and 2. The other compounds in Table 1 have a single bond at that position.

Processes for preparing compounds of formula (I) and formula (II) are provided as further embodiments of the invention and are illustrated by the following procedures in which the meanings of the generic radicals are as given above unless otherwise qualified. Specifically, the compounds of formula (I) or formula (II) can be prepared from convenient starting materials, employing procedures (e.g., reagents and reaction conditions) known to those of skill in the art. For example, suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms, and Structure*, Second Edition, March (1977); Greene, T. W.; Wutz, P. G. M. *Protecting Groups In Organic Synthesis*, Second Edition, 1991, New York, John Wiley & sons, Inc.; and *Comprehensive Organic Transformations*, Second Edition, Larock (1999). Additionally, specific exemplary procedures are shown in the examples herein below.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I or II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I or II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I or II can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I or II in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as an antibacterial agent may be determined using pharmacological models which are well known to the art, including the tests described in the Examples below.

The compounds of the invention may be also be useful as pharmacological tools for the further investigation of the mechanism of their antibacterial action.

The compounds of the invention can also be administered in combination with other therapeutic agents that are effective to treat bacterial infections, or to inhibit or kill a bacteria.

The system used to name the compounds of the invention will be clear to one of skill in the art based on the following examples. Names generally consist of the base structure, e.g., betulin, allobetulin, or lupeol, followed by a substituent. For example, betulin-28-succinate, with the structure shown in Example 1, consists of a succinic acid molecule esterified to the hydroxyl at carbon 28 of betulin. If no number is given for the substituent, the substitent is attached to the hydroxyl at carbon 3 on the base structure.

Betulin-3-glycerol oxalate is a compound of formula (I), wherein $R_4$ and $R_5$ together are hydroxyl, $R_2$ and $R_3$ together are —OC(=O)C(=O)OCH$_2$CH(OH)CH$_2$OH, and $R_1$ is hydrogen. Betulin-1-ene-2-ol is a compound of formula (I), wherein the bond between carbons 1 and 2 is a double bond, $R_1$ is hydroxyl, $R_2$ and $R_3$ together are hydroxymethyl, and $R_4$ and $R_5$ together are oxo. Uvaol is a compound of formula (II), wherein $R_{10}$ is methyl, $R_9$ is hydrogen, $R_8$ is methyl, $R_7$ is hydrogen, $R_{11}$ is hydroxymethyl, $R_6$ is absent and the bond between carbons 12 and 13 is double, $R_3$ is hydrogen, $R_4$ and $R_5$ are methyl, $R_2$ is hydrogen, and $R_1$ is hydroxy. Oleanolic acid has the same structure as uvaol, except it has a carboxy at $R_{11}$ instead of hydroxymethyl. The structure of hederin hydrate is disclosed at page 871 of the Aldrich Chemical Co. 2000–2001 catalog. The structure of other named compounds can be found in standard sources such as the *Merck Index*. "Betulin arabinose galactan" refers to betulin in a solution of arabino-galactan.

Unless otherwise stated, amino acid substituents are attached to the compounds of the invention through their carboxyl groups via ester linkages. Thus, betulin-3,28-diglycine is the same compound as betulin-3,28-diglycine ester.

The invention will now be illustrated by the following non-limiting Examples.

EXAMPLES

Example 1

Betulin-28-succinate

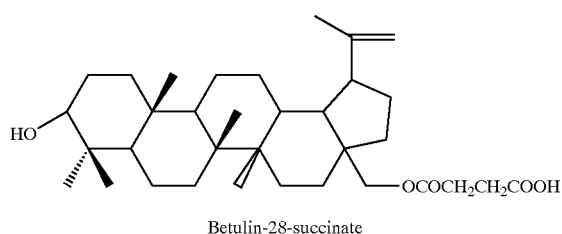

Betulin-28-succinate m=0.200 g
$C_{34}H_{54}O_5$
Exact Mass: 542.40
Mol. Wt.: 542.79
C, 75.23; H, 10.03; O, 14.74

Place Betulin 1.00 g (1 equivalent) along with Succinic anhydride 0.249 g (1.1 equivalent) and imidazole 0.462 g (3 equivalent) in a 25 ml flask. Add 20 ml dried dichloromethane, stir and reflux for 24 hours. After the reaction completes, add 10 ml 3% HCl, shake gently. The pH should be 2. Separate the organic part. Use dichloromethane (3×5 ml) to extract the water layer. Combine the organic part and use 3% HCl (2×10 ml) to wash it. Use $Na_2SO_4$ (anhy.) to dry the organic part. Evaporate the solvent, get white powder 1.10 g. Use small amount of acetone to tritrate the white product. After drying, get 0.90 g white granular solid with yield 73.2%. M.P.: 234.1–235.5° C.;1R(KBr): 3355.76, 2953.19, 1734.29, 1708.63, 1264.63, 1174.11 cm$^{-1}$; $^1$H NMR (CDCl$_3$): δ4.69 (S, 1H), 4.59 (S, 1H), 4.32 (D, J=11.1 Hz, 1H), 3.91 (D, J=11.1 Hz, 1H), 3.22 (M, 1H), 2.68 (M, 4H), 2.44 (M, 1H), 1.68 (S, 3H), 0.76, 0.82, 0.97, 1.02 (All S, 4×3H), 0.71–2.1 (complex, 28H); $^{13}$C NMR (CDCl$_3$): 172.43, 167.96, 145.61, 105.38, 74.56, 58.71, 50.80, 45.88, 44.32, 43.21, 41.94, 38.21, 36.38, 34.36, 34.21, 33.12, 32.66, 30.01, 29.68, 25.23, 25.08, 24.57, 24.37, 23.50, 22.87, 22.54, 20.71, 16.30, 14.67, 13.79, 11.62, 11.54, 10.89, 10.30;

Example 2

Betulin-3,28-disuccinate

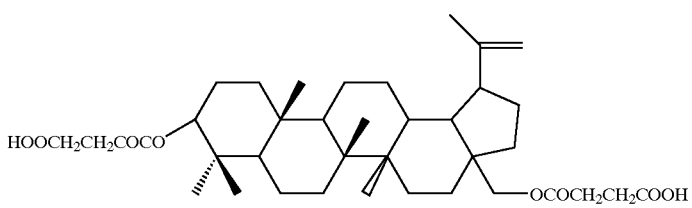

Betulin-3,28-disuccinate m=0.200 g
$C_{38}H_{58}O_8$
Exact Mass: 642.41
Mol Wt.: 642.86
C, 71.00; H, 9.09; O, 19.91

Place 0.5 g Betulin along with 0.34 g succinic anhydride and 0.46 g imidazole in a 25 ml flask. Add 15 ml CH$_2$Cl$_2$ (dried) and reflux for 12 hours. Add 10 ml 3% HCl, separate the organic part, use CH$_2$Cl$_2$ (3×5 ml) to wash, and combine the organic parts. Use 3% HCl (2×10 ml) wash the organic part, then use Na$_2$SO$_4$ to dry it. Evaporating the solvent gives 0.73 g yellow powder. Useing CHCl$_3$— hexane to crystalize gives 0.65 g yellow powder. Or stiring the solid with 3% HCl in the warm condition for 12 hours, followed by filtration and drying, gives 0.60 g powder with yield 82.5%. M.P. (decomp.) 116.1–117.8° C.; IR(KBr): 2954.83, 1726.44, 1169.46 cm$^{-1}$; $^1$H NMR (CDCl$_3$): 4.69 (S, 1H), 4.59 (S, 1H), 4.51 (M, 1H), 4.31 (D, J=11.4 Hz, 1H), 3.88 (D, J=10.8 Hz, 1H), 2.67 (M, 8H), 2.44 (M, 1H), 1.68 (S, 3H), 1.3, 0.98, 0.85, 0.86, 0.79 (all S, 5×3H), 1.06–2.1 (complex, 24H); $^{13}$C NMR (CDCl$_3$): 173.73, 173.65, 167.98, 167.37, 145.63, 105.44, 77.09, 58.72, 50.91, 45.77, 44.30, 43.25, 41.94, 38.22, 36.40, 33.88, 33.36, 33.10, 32.56, 29.97, 29.61, 25.18, 24.87, 24.61, 23.41, 22.54, 20.67, 19.13, 16.34, 14.65, 13.69, 12.04, 11.68, 11.55, 1031;

Example 3

Betulin-28-phthalate

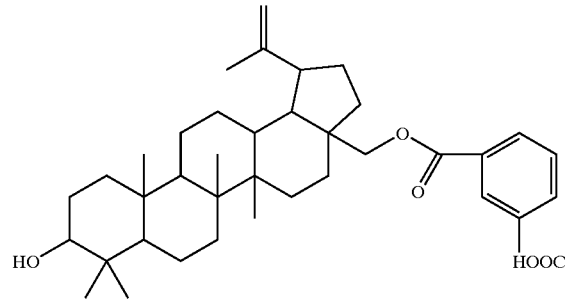

Betulin-28-phthalate $C_{38}H_{54}O_5$
Exact Mass: 590.40
Mol. Wt.: 590.83
C, 77.25; H, 9.21; O, 13.54

Place Betulin 1 g (I equivalent) and imidazole 0.31 g (4equivalents) with phthalic anhydride 0.35 g (1.05 equivalents) in a 15 mL flask. Add 5 mL of 1-methyl-2- pyrrotidinone and stir at room temperature for 48 hours. Pour the mixture into the water with strong stirring and adjust pH around 3. Stir for 2–3 hours. All the chunks should become small particles. After filtration, use water to wash three times, and then dry it in the oven. Get 1.25 g white solid. Use ethyl acetate: Hexane (1:4) to elute the product from the silica gel column and get 0.69 g white prism solid. Yield is 51.5%. M.P.: 205.2–206.9° C. JR(cm$^{-1}$): 3500.0, 2957.0, 2876.4, 1719.7, 1458.2, 1386.5, 1289.8, 1136.8, 1072.4; $^1$H NMR(CDCl$_3$, ppm): 7.93 (D, 1H, J=6.9 Hz),7.73 (D, 1H, J=6.6 Hz), 7.59 (M, 2H), 4.71 (S, 1H), 4.60 (S, 1H), 4.53 (D, 1H, J=8.4 Hz), 4.14 (D, 1H, J=10.8 Hz), 3.22 (M, 1H), 2.51 (M, 1H), 1.69 (S, 3H), 1.05, 0.97, 0.95, 0.82, 0.76 (all S, 5×3H), 2.2–0.6 (Complex, 26H); $^{13}$C NMR (CDCl$_3$, ppm): 171.85, 169.03, 150.46, 133.90, 132.46, 131.13, 130.35, 129.19, 110.25, 79.43, 66.23, 64.90, 55.60, 50.69, 49.26, 48.08, 46.83, 43.07, 41.12, 39.18, 39.04, 38.01, 37.48, 34.92, 34.41, 30.11, 29.92, 28.34, 27.69, 27.37, 25.54, 21.14, 19.53, 18.58, 16.45, 16.38, 15.75, 15.61, 15.14.

Example 4

Lupeol-3-phthalate

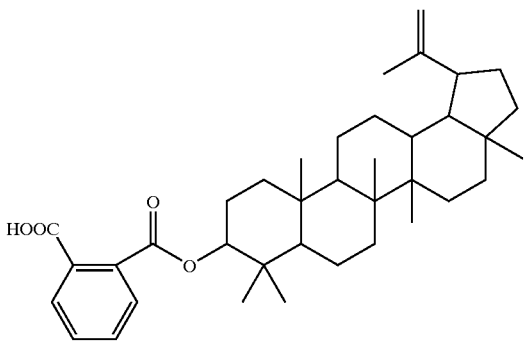

Lupeol-3-phthalate

C$_{38}$H$_{54}$O$_4$

Exact Mass: 574.40

Mol. Wt.: 574.83

C, 79.40; H, 9.47; O, 11.13

Place Lupeol 0.100 g and imidazole 0.96 g with 0.069 g phthalic anhydride in a 25 mL flask, add dried dichloromethane 10 mL and reflux for 24 hours. Then use 3% HCl (3×5 mL) to wash the organic part, which is followed by drying with, sodium sulfate (anhy.). After evaporate the solvent, receive white powder, which is followed by stirring with 3% HCl for 12 hours. Then filter and dry the white solid in the oven. This results in 0.128 g white product with 94.8% yield. M.P.: 160.2–162.1° C. $^1$H NMR (CDCl$_3$, ppm): 7.96 (D, 1H, J-6.9 Hz), 7.79 (D, 1H, J=6.0 Hz), 7.63 (M, 2H), 4.79 (M, 1H), 4.74 (S, 1H), 4.63 (S, 1H), 2.44 (M, 1H), 1.74 (S, 3H), 1.46, 1.08, 1.00, 0.93, 0.91, 0.84 (S, 6×3H), 2.1–0.7 (Complex, 25H). $^{13}$C NMR (CDCl$_3$, ppm): 172.05, 168.19, 151.29, 133.74, 132.25, 131.23, 130.79, 130.35, 129.37, 109.73, 83.59, 55.91, 50.73, 48.67, 48.37, 43.37, 43.21, 41.24, 40.37, 38.81, 38.43, 37.48, 35.94, 34.59, 30.21, 28.40, 27.81, 25.47, 23.51, 21.35, 19.66, 18.56, 18.37, 16.99, 16.51, 16.35, 14.91.

Example 5

Lupeol-3-succinate

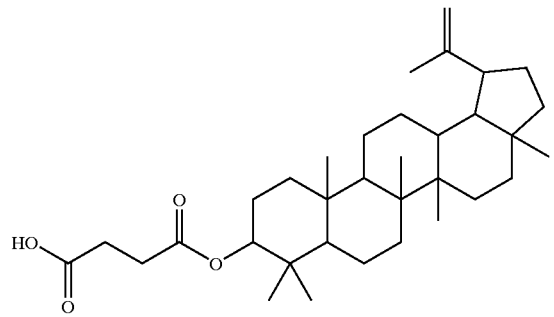

Lupeol-3-succinate

C$_{34}$H$_{54}$O$_4$

Exact Mass: 526.40

Mol. Wt.: 526.79

C, 77.52; H, 10.33; O, 12.15

Place Lupeol 100 mg (1 equivalence) and succinic anhydride 0.070 g (3 equivalence) with imidazole 0.016 g (1 equivalence) in a 25 mL flask. Add dried dichloromethane 10 mL, then reflux for 48 hours. After the reaction is done, add sodium bicarbonate saturated water solution 1 mL, separate the organic part, and extract the water phase with dichloromethane (3×5 mL). Then use 3% HCl (3'10 mL) to wash the organic part, which is followed by drying with sodium sulfate (anhy.). Evaporating the solvent gives a white powder, which is stirred with 3% HCl 15 mL overnight, which is followed by filtration and drying in the oven. 0.12 g white powder is obtained with 97.6% yield. M.P.: 224.7–226.3° C. $^1$H NMR; 4.69 (S, 1H), 4.57 (S, 1H) 4.501 (M, 1H), 2.66 (M, 4H), 2.39 (M, 1H), 1.68 (S, 3H), 1.36, 1.03, 0.94, 0.85, 0.83, 0.79 (S, 6×3H), 1.8–0.7 (Complex, 25H), $^{13}$C NMR (CDCl$_3$, ppm): 174.13, 168.54, 147.54, 105.94, 78.14, 51.94, 46.87, 44, 83, 44358, 39.56, 39.39, 37.40, 36.57, 34.91, 34.59, 34.41, 33.62, 32.13, 30.75, 26.39, 26.00, 25.72, 24.47, 23.99, 21.64, 20.21, 17.51, 15.86, 14.75, 14.58, 13.09, 12.74, 12.54, 11.09.

Example 6

3-Allobetulon-1-en-2succinate

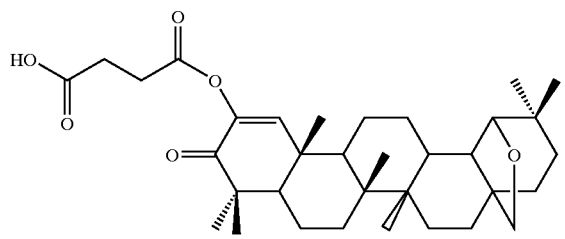

3-Allobetulon-1-en-2-succinate

C$_{34}$H$_{50}$O$_6$

Exact Mass: 554.36

Mol. Wt.: 554.76

C, 73.61; H, 9.08; O, 17.30

Place 0.5 g 3-Allobetulon-1-en-2-ol (1 equivalent) and 0.33 g succinic anhydride (3 equivalents) with 0.13 g 4-(dimethylamino)-pyridine (1 equivalent) in a 25 mL flask. Add 10 mL acetonitrile and reflux for 48 hours, which is followed by adding 15 mL chloroform. Use 10 mL 3% HCl to wash the organic part three times, which is followed by drying with sodium sulfate (anhy.). Evaporating the solvent gives 0.55 g crude product. Use silica gel column to separate the crude product with solvent hexane: diethyl ether (3:1), which results in 0.303 g white amorphous solid withyield 49.7%. M.P.: 178.1–180.4° C. IR (cm$^{-1}$); 2944.6, 2866.3, 1764.8, 1695.4, 1139.5; $^1$H NMR (CDCl$_3$, ppm): 6.83 (S, 1H) 3.80 (D, 1H, J=7.8 Hz), 3.59 (S 1H), 3.49 (D, 1H, J=7.8 Hz), 2.82 (M 4H), 1.19, 1.17, 1.13, 1.05, 0.91, 0.82 (all S, 6×3H), 1.8–0.8 (Complex, 23H); $^{13}$C NMR (CDCl$_3$, ppm): 198.10, 176.47, 170.86, 145.43, 143.16, 88.23, 71.52, 53.44, 46.99, 45.82, 45.40, 41.82, 41.84, 41.37, 40.07, 36.98, 36.58, 34.57, 33.54, 33.00, 29.10, 28.89, 28.79, 28.21, 26.66, 26.51, 24.89, 21.67, 20.52, 19.26, 16.49, 13.74.

Example 7

Allobetulin-3-diglycolate

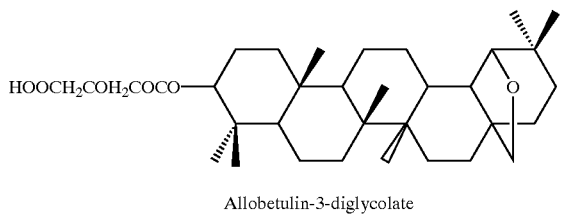

Allobetulin-3-diglycolate m=0.300 g

C$_{34}$H$_{54}$O$_6$

Exact Mass: 558.39

Mol. Wt.: 558.79

C, 73.08; H, 9.74; O, 17.18

In 25-mL flask, stir diglycolic anhydride 0.39 g and 0.5 g allobetulin in 15 mL CHCl$_3$. Then reflux for 24 hours. Add 10 mL saturated NaHCO$_3$, shake gently. Then separate the organic part, use the CHCJ$_3$ (2×5 ml) to wash, and combine the organic parts. Use 3% HCl (10 ml) and water (2×10 ml) to wash it. Then use Na$_2$SO$_4$ (anhy.) to dry the organic part. Evaporating the solvent yields 0.57 g of white granular solid with yield 90.2%. M.P.: 285.2 (decompose). IR (KBr): 2964.07, 1753.33, 1223.67, 1110.16 cm$^{-1}$; $^1$H NMR (CDCl$_3$); δ 4.64 (DD, 1H), 4.32 (S, 4H), 3.66 (D, 1H, J=9 Hz), 3.54 (S, 1H), 3.46 (D, 1H, J=9 Hz), 0.97, 0.926, 0.891, 0.866, 0.852, 0.828, 0.796 (all S, 7×3H), 1.1–1.9 (complex CH—, CH$_2$, 24H); $^{13}$C NMR (CDCl$_3$): δ 171.28, 88.342, 83.431, 71.597, 69.498, 55.872, 51.339, 47.164, 41.837, 41.094, 40.985, 38.886, 38.289, 37.509, 37.079, 36.627, 34.478, 34.157, 33.057, 29.166, 28.408, 26.775, 26.601, 24.917, 24.072, 21.391, 18.476, 16.916, 16.064, 13.87.

Example 8

Allobetulin-3-glutarate

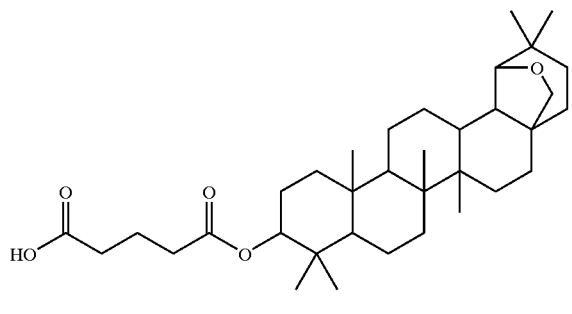

Allobetulin-3-glutarate

C$_{35}$H$_{56}$O$_5$

Exact Mass: 556.41

Mol. Wt.: 556.82

C, 75.50; H, 10.14; O, 14.37

Place 1 g Allobetulin (1 equivalent) and 0.52 g glutaric anhydride (2 equivalents) with imidazole 0.92 g (6 equivalence) in a 15 mL flask. Add 4.5 mL 1-methyl-2-pyrrolidinone and stir for 48 hours at 70° C. Pour the reaction mixture into 150 mL water. Adjust the pH to around 2. Stir for 3–4 hours and all the chunks should be broken into small particles. After filtration, dry the crude product in the oven. Crystalizing the crude product with chloroform and hexane yields 1.11 g of white amorphous product with yield 88.1%. M.P.: 283,2–284.9° C. IR (cm$^{-1}$): 2948.9, 1724.7, 1458.9, 1281.8,1217.4; $^1$H NMR (CDCl$_3$, ppm): 4.50 (M, 1H), 3.80 (D, 1H, J=8.1 Hz), 3.55 (S, 1H), 3.46 (D, 1H, J=7.8 Hz), 2.46 (M, 4H), 1.99 (M, 2H), 0.98, 0.93, 0.92, 0.87, 0.84, 0.80 (all S, 6×3H), 1.8–0.8 (Complex, 28H); $^{13}$C NMR (CDCl$_3$, ppm): 177.86, 173.08, 88.34, 81.44, 71.60, 55.92, 51.35, 47.18, 41.84, 41.09, 40.99, 38.93, 38.22, 37.53, 37.09, 36.63, 34.49, 34.20, 34.06, 33.31, 33.06, 29.17, 28.36, 26.79, 26.62, 24.92, 24.10, 21.38, 20.43, 18.51, 16.95, 16.07, 13.87.

Example 9

Allobetulin-3-phthalate

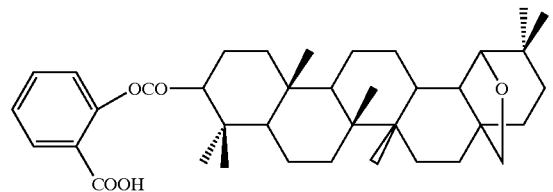

Allobetulin-3-phthalate m=0.300 g

C$_{38}$H$_{54}$O$_5$

Exact Mass: 590.40

Mol. Wt.: 590.83

C, 77.25; H, 9.21; O, 13.54

In 25-ml flask, stir phthalic anhydride 0.20 g and imidazole 0.38 g in 10 ml CH$_2$Cl$_2$, add the 0.5 g Allobetulin into the flask, and then reflux for 6 hours. Add 10 ml saturated sodium bicarbonate water solution into the flask, dissolve the solid, separate the organic part, use the CH$_2$Cl$_2$ (3×5 ml)

wash and combine the organic parts. Use 3% HCl (3×10 ml) wash again. Use Na$_2$SO$_4$ (anhy.) to dry the organic part. Evaporate the solvent, get white solid 0.60 g with yield 89.6%. M.P.: 252.3–253.9° C.; IR (KBr): 2948.90, 2868.36, 1724.74, 1660.31, 1458.97, 1289.84, 1136.82, 1072.39, 975.75 cm$^{-1}$; $^1$H NMR (CDCl$_3$): δ 7.91 (D, J=6.6 Hz, 1H), 7.73 (D, J=6.9 Hz, 1H), 7.58 (M, 2H), 4.78 (M, 1H), 3.80 (D, 1H, J=7.8 Hz), 3.62 (S, 1H), 3.48 (D, J=7.8 Hz, 1H), 2.0–0.8 (complex, 45H); $^{13}$C NMR (CDCl$_3$): 166.47, 163.55, 129.22, 127.32, 126.21, 125.98, 125.44, 124.28, 83.47, 78.42, 66.75, 51.23, 46.53, 42.31, 37.02, 36.25, 36.16, 34.15, 33.60, 32.72, 32.24, 31.77, 29.66, 29.37, 28.24, 24.31, 23.57, 21.96, 21.77, 20.08, 18.62, 16.60, 13.67, 12.19, 12.12, 11.26, 9.06.

Example 10

Allobetulin-3-succinate

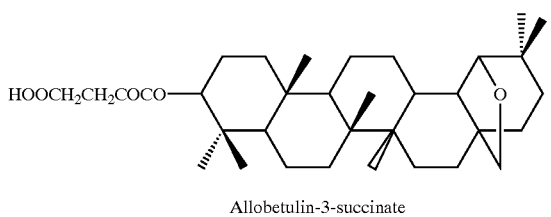

Allobetulin-3-succinate m=0.300 g

C$_{34}$H$_{54}$O$_5$

Exact Mass: 542.40

Mol. Wt.: 542.79

C, 75.23; H, 10.03; O, 14.74

In 25-ml flask, stir succinic anhydride 0.23 g and imidazole 0.46 g in 15 ml CH$_2$Cl$_2$, add 0.5 g allobetulin into the flask, and then reflux for 24 hours. Add 10 ml saturated sodium bicarbonate to dissolve the solid, then separate the organic part, use CH$_2$Cl$_2$ (2×5 ml) to wash and combine the organic parts. Use 3% HCl (2×10 ml) to wash the organic part. Use Sodium sulfate (anhy.) to dry the organic part. Evaporating the solvent results in a white granular solid. Stir the crude product in 3% HCl for 12 hours, after filtration, which gives 0.48 g of a white solid, with yield 78.7%. M.P.: (decomp.) 258.1–259.5° C.; IR (KBr): 2940.85, 2868.36, 1732.79, 1450.91, 1386.49, 1225.41, 1169.04 cm$^{-1}$; $^1$H NMR (CDCl$_3$): δ 4.52 (M, 1H), 3.78 (D, J=7.5 Hz, 1H), 3.55 (S, 1H), 3.45 (D, J=7.5 Hz, 1H), 2.65 (M, 4H), 0.76, 0.78, 0.84, 0.86, 0.90, 0.92, 1.0 (all S, 7×3H), 1.1–1.9 (complex, 24H); $^{13}$C NMR (CDCl$_3$): 172.78, 167.44, 83.50, 77.00, 66.73, 51.10, 46.50, 42.31, 36.99, 36.14, 34.08, 33.38, 32.67, 32.23, 31.77, 29.62, 29.35, 28.21, 24.93, 24.56, 24.32, 23.41, 21.94, 21.76, 20.08, 19.14, 16.54, 13.65, 12.07, 11.22, 9.04.

Example 11

Betulin-3,28-didiglycolate

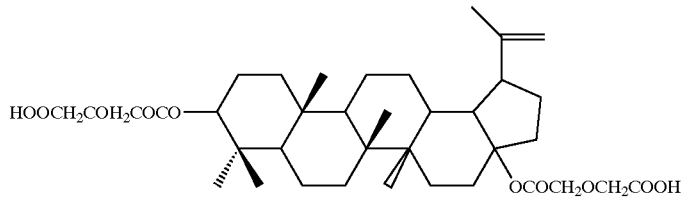

Betulin-3,28-didiglycolate m=0.200 g

C$_{38}$H$_{58}$O$_{10}$

Exact Mass: 674.40

Mol. Wt.: 674.86

C, 67.63; H, 8.66; O, 23.71

In 15-ml flask, stir diglycolic anhydride 0.78 g and imidazole 0.92 g in 4.5 ml 1-methyl-2-pyrrolidinone at 70° C. After they dissolve add 1 g Betulin. Stir for 24 hours. Pour mixture slowly into 180 ml water, adjust the pH to 2, stir the water solution until all the precipitate forms small granules. After the filtration, use 1% HCl, water to wash the product. Drying gives 1.45 g granular product (little brown color) with yield 94.8%. M.P. (decomp.) 137.8–139.2° C.; IR (KBr): 2961.07, 1747.02, 1220.45, 1144.87 cm$^{-1}$, $^1$H NMR (CDCl$_3$): δ 4.71 (S, 1H), 4.61 (complex, 2H), 4.2–4.45 (complex, 9H), 3.96 (D, J-11.4 Hz), 2.45 (M, 1H), 1.70 (S, 3H), 0.83, 0.85, 0.97, 1.04, (S, 4×3H), 1.05–2.10 (complex, 28H); $^{13}$C NMR (CDCl$_3$): 168.46, 168.29, 166.50, 166.17, 145.34, 105.65, 78.48, 64.66, 64.39, 64.28, 59.60, 50.83, 45.75, 44.28, 43.20, 41.94, 38.23, 36.40, 33.83, 33.43, 33.14, 32.56, 29.99, 29.58, 25.16, 23.57, 22.52, 20.61, 19.23, 16.31, 14.62, 13.66, 12.02, 11.68, 11.54, 10.27.

Example 12

Betulin-28-diglycolate

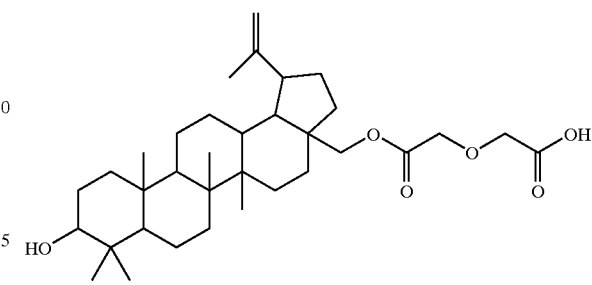

Betulin-28-diglycolate

C$_{37}$H$_{54}$O$_6$

Exact Mass: 558.39

Mol. Wt.: 558.79

C, 73.08; H, 9.74; O, 17.18

Place Betulin 0.5 g (1 equivalent) and diglycolic anhydride 0.14 g (1.02 equivalents) with imidazole 0.31 g (4 equivalents) in a 15 mL flask. Add 4 mL 1-methyl-2- pyrrolidinone and stir 48 hours at room temperature. Pour the mixture into 150 mL water, which is followed by adjusting pH to around 2. Stir for 2–3 hours. All the chunks should be broken to small particles. After filtration, dry the crude product in the oven, which is followed by passing through a silica gel column with hexane: diethyl ether (3:1). This yielded 0.43 g white prizm solid with yield 68.3%. M.P.: 219.2–220.2° C. IR (cm$^{-1}$): 3454.5, 2941.1, 1759.5, 1729.44, 1216.3, 1136.8, $^1$H NMR (CDCl$_3$, ppm): 4.74 (S, 1H), 4.65 (S, 1H), 4.48 (D, 1H, J=11.1 Hz), 4.33 (S, 4h), 4.05 (D, 1H, J=11.1 Hz), 3.27 (M, 1H), 2.49 (M, 1H), 1.73 (S, 3H), 1.08, 1.02, 1.01, 0.87, 0.81 (all S, 5×3H), 2.2–0.6 (Complex, 25H); $^{13}$C NMR (CDCl$_3$, ppm): 172.16, 171.55, 150.19, 110.46, 79.44, 69.60, 69.32, 64.58, 55.64, 50.69, 49.15, 48.02, 46.79, 43.06, 41.23, 39.21, 39.05, 38.01, 37.50, 34.83, 34.53, 30.01, 29.82, 28.34, 27.68, 27.36, 25.52, 21.11, 19.49, 18.64, 16.47, 16.39, 15.74, 15.14.

Example 13

Betulin-3,28-diglutarate

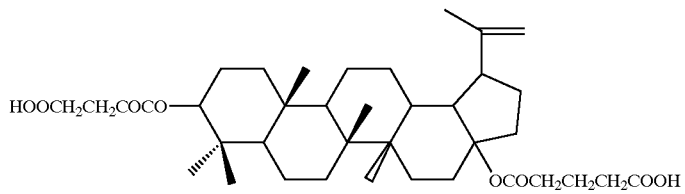

Betulin-3,28-diglutarate m=0.300 g $C_{40}H_{62}O_8$

Exact Mass: 670.44

Mol. Wt.: 670.92

C, 71.61; H, 9.31; O, 19.08

In 15-ml flask, stir glutaric anhydride 1.29 g and imidazole 1.54 g in 4.5 ml 1-methyl-2-pyrrolidinone at 70° C. After they dissolve add 1 g betulin. Stir for 48 hours. Pour mixture slowly into 180 ml water, adjust the pH to 2, and stir the water solution until all the precipitate forms small granules. After the filtration, use 1% HCl in water to wash the product. Drying results in 1.22 g gray solid powder with yield 80.3%. M.P. (decomp.): 104.5–106.2° C.; IR (KBr): 2956.95, 2876.42, 1732.79, 1458.97, 1386.49, 1201.25, 991.85 cm$^{-1}$; $^1$H NMR (CDCl$_3$): δ 4.69 (S, 1H), 4.49 (S,1H), 4.50 (M, 1H), 4.29 (D, 1H, J=10.5 Hz), 3.85 (D, 1H, J=11.1 Hz), 2.42 (M, 9H), 1.98 (M, 5H),1.68 (S, 3H), 0.75–1.9 (complex, 39H); $^{13}$C NMR (CDCl$_3$): 178.947, 173.693, 173.059, 150.463, 110.297, 81.478, 63.217, 55.712, 50.618, 49.132, 48.082, 46.741, 43.054, 41.247, 38.711, 38.194, 37.924, 37.414, 34.937, 34.449, 34.026, 33.669, 33.370, 30.120, 29.916, 28.371, 27.388, 25.493, 24.087, 21.157, 20.385, 20.254, 19.481, 18.519, 16.938, 16.516, 16.392, 15.109.

Example 14

Betulin-28-glutarate

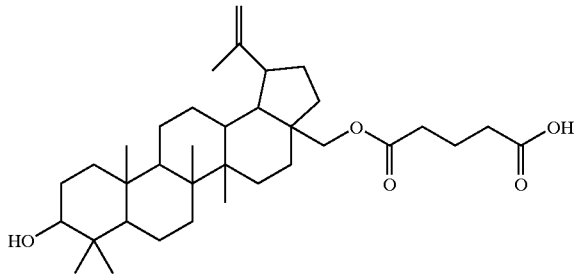

Betulin-28-glutarate $C_{35}H_{56}O_5$

Exact Mass: 556.41

Mol Wt.: 556.82

C, 75.50; H, 10.14; O, 14.37

Place 1 g of Betulin (1 equivalent) and 0.271 g glutaric anhydride (1.05 equivalents) with 0.615 g imidazole (4 equivalents) in a 25 mL flask, add 4 mL 1-methyl-2-pyrrolidinone and stir for 48 hours at room temperature. Pour the mixture in 150 ml. water, while stirring. Then adjust pH to around 3. Break the big chunks to small particles, which is followed by filtration and drying in the oven. The crude products are passed through the silica gel column with diethyl ether: hexane (1:3). This results in 0.765 g white prism solid with a yield of 60.7%. M.P.: 204.3–206.1° C. IR (cm$^{-1}$): 3438.7, 2962.4, 2870.5, 1741.7, 1717.1, 1463.0, 1395.2; $^1$H NMR (CDCl$_3$, ppm): 4.73 (S, 1H), 4.64 (S, 1H), 4.35 (D, 1H, J=11.1 Hz), 3.93 (D, 1H, J=11.1 Hz), 3.25 (M, 1H), 2.50 (M, 5H), 1.73 (S, 3H), 1.08, 1.02, 0.87, 0.81 (all S, 4×3H), 2.2–0.8 (Complex, 30H); $^{13}$C NMR (CDCl$_3$, ppm): 177.72, 173.67, 150.49, 110.25, 79.39, 63.202, 55.65, 50.72, 49.15, 48.06, 46.75, 43.06, 41.23, 39.22, 39.05, 37.94, 37.51, 34.94, 33.68, 33.16, 30.14, 29.94, 28.35, 27.73, 27.40, 25.55, 21.14, 20.27, 19.51, 18.65, 16.47, 16.40, 15.74, 15.14.

Example 15

Betulin-3,28-dimaleate

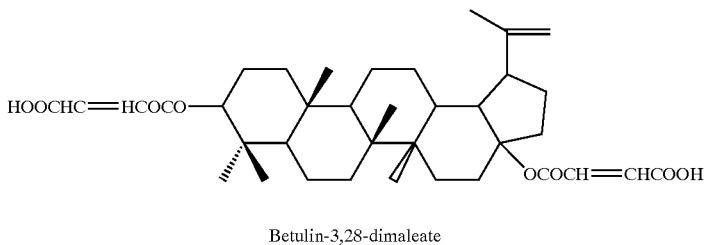

Betulin-3,28-dimaleate m=0.300 g
$C_{38}H_{54}O_8$
Exact Mass: 638.38
Mol. Wt.: 638.83
C, 71.44; H, 8.52; O, 20.04

In 50-ml flask, stir maleic anhydride 11.09 g and Betulin 5 g in 20 ml 1-methyl-2-pyrrolidinone at 70° C. for 48 hours. Pour the mixture slowly into 800 ml water, adjust the pH to 3, and stir the water solution until all the precipitation forms small granules. After the filtration, use 1% HCl, in water to wash the product. Drying gives 6.50 g gray solid granules with yield 90.1%. M.P.: 181.4–182.9° C.; IR (KBr): 2952.27, 1738.94, 1700.43, 1635.34, 1239.03, 994, 826 cm$^{-1}$; $^1$H NMR (CDCl$_3$): 6.55–6.40 (M, 4H), 4.76–4.67 (complex, 3H), 4.56 (D, J=11.1 Hz, 1H), 4.09 (D, J=10.5 Hz, 1H), 2.45 (M, 1H), 1.70 (S, 3H), 0.78, 0.81, 0.90, 1.02, 1.10 (all S, 5×3H), 1.12–2.1 (complex, 24H); $^{13}$C NMR (CDCl$_3$): 163.80, 163.41, 159.92, 159.76, 145.10, 132.64, 132.20, 125.13, 124.76, 105.80, 80.56, 61.43, 50.83, 45.73, 44.30, 43.19, 41.94, 38.26, 36.40, 34.38, 33.80, 33.45, 33.23, 32.57, 29.90, 29.55, 25.04, 24.92, 23.50, 22.48, 20.59, 18.89, 16.30, 14.63, 13.63, 11.97, 11.68, 11.55, 10.90, 10.30.

Example 16

Betulin-28-maleate

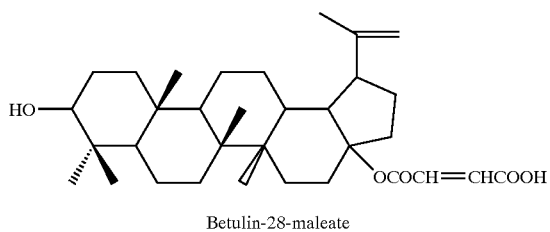

Betulin-28-maleate m=0.300 g
$C_{34}H_{52}O_5$
Exact Mass: 540.38
Mol. Wt.: 540.77
C, 75.51; H, 9.69; O, 14.79

In 500-ml flask, stir maleic anhydride 3.33 g and 10 g Betulin in 200 ml CHCl$_3$. Reflux for 40 hours. Add 50 mL 3% HCl, separate the organic part, use CHCl$_3$ (3×20 mL) to wash the aqueous phase, and combine the organic parts. Use 3% HCl (2×50 mL) to wash the organic phase, which is followed by using Na$_2$SO$_4$ (anhydrous) to dry organic part. After evaporating the solvent, use THF-hexane to crystalize the crude product. This gives 9.2 g white product with yield 75.2%, M.P.: 242.5–243.6° C.; IR (KBr): 3416.01, 2948.90, 2868.36, 1716.69, 1652.26, 1265.68, 1233.47 cm$^{-1}$; $^1$H NMR(CDCl$_3$): δ 6.5 (Q, 2H), 4.78 (S, 1H), 4.68 (S, 1H), 4.56 (D, J=11.1 Hz, 1H), 4.12 (D, J=11.1 Hz, 1H), 3.26 (M, 1H), 2.50 (M, 1H), 1.76 (S, 3H), 0.84, 0.90, 1.05, 0.06, 1.10 (S, 5×3H), 2.1–0.8 (complex, 25H); $^{13}$C NMR(CDCl$_3$): 163.901, 159.57, 145.15, 132.58, 124.62, 105.75, 74.52, 61.44, 50.81, 45.85, 44.35, 43.18, 41.96, 38.25, 36.40, 34.39, 34.23, 33.27, 32.67, 29.91, 29.69, 25.09, 24.94, 23.51, 22.88, 22.50, 20.68, 16.27, 14.65, 13.80, 11.64, 11.56, 10.90, 10.33.

Example 17

Betulin-3,28-diphthalate

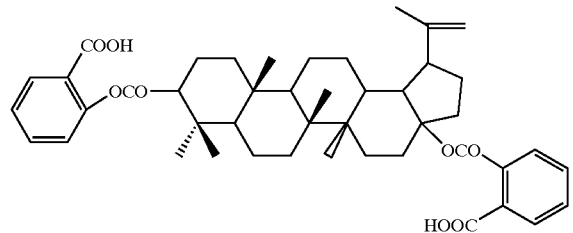

Betulin-3,28-diphthalate m=0.300 g
$C_{46}H_{58}O_8$
Exact Mass: 738.41
Mol. Wt.: 738.95
C, 74.77; H, 7.91; O, 17.32

In 50-ml flask, stir phthalic anhydride 8.37 g and imidazole 7.69 g in 20 ml 1-methyl-1-pyrrolidinone at 70° C. After they dissolve, add 5 g betalin. Stir for 48 hours. Pour mixture slowly into 800 ml water, adjust the pH to 2, and stir the water solution until all the precipitate forms small granules. After the filtration, use 1% HCl in water to wash the product. Drying gives 7.59 g granules (light yellow color) with yield 90.8%. M.P. (decomp.) 166.8–168.6° C.; IR (KBr): 2956.95, 2876.42, 1716.69, 1394.54, 1281.79, 128.77, 1088.50, 991.85, 742.19 cm$^{-1}$; $^1$H NMR (CDCl$_3$): δ 7.87 (M 2H), 7.77 (M, 2H), 7.58 (M, 4H), 4.76–4.53 (complex, 4H), 4.08 (D, J=10.2 Hz, 1H), 2.50 (M, 1H), 1.68 (S, 3H), 0.82, 0.84, 0.90, 1.02, 1.08 (all S, 5×3H), 1.1–2.2 (complex, 24H); $^{13}$C NMR (CDCl$_3$): 168.57, 168.33, 163.68, 162.99, 145.58, 128.79, 128.23, 127.37, 126.56, 126.39, 126.32, 126.19, 125.22, 125.08, 124.69, 124.50, 105.47, 78.49, 60.12, 51.04, 45.80, 44.46, 43.36, 42.09, 39.22, 38.27, 36.40, 33.99, 33.56, 33.24, 32.62, 29.96, 29.53, 25.12, 23.55, 22.58, 20.68, 18.72, 16.42, 14.62, 13.66, 12.20, 11.72, 11.56, 10.48.

Example 18

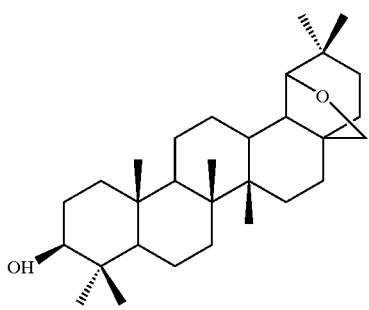

Allobetulin,
oleanan-3β-ol-28,19-β-ether

In 100-ml flask stir 2 g of Betulin in 50 ml of $CH_2Cl_2$ at 0° C. Add 5 ml of 99% $CF_3COOH$ and stir for 30 minutes. Pour reaction mixture in 100 ml of cracked ice and separate the organic part. Extract with $CH_2Cl_2$ (3×10 ml) and wash combined organic extracts with conc. $NaHCO_3$ (2×20 ml) and water (2×20 ml), and dry the extract over $Na_2SO_4$ (anh.). Evaporation of solvent gives 1.98 g of Allobetulin, which was recrystallized from hexane-dichloromethane to yield white needles mp. 268–269° C. [lit. 265–268], IR (KBr) 3448.5, 2941.5, 2866.6, 1780.7, 1456.6, 1384.4, 1168.9, 1035.0, cm$^{-1}$; $^1$H NMR (CDCl$_3$) d 3.75 (D, J=10.3 Hz, 1H, 28-H), 3.51 (S, 1-H, 19-H), 3.41 (D, J=10.3 Hz, 1H, 28-H), 3.18 (DD, 1H, 3-H), 0.74, 0.76, 0.81, 0.88, 0.89, 0.94, 0.94 (all S, 7×3H, 27-, 23-, 24-, 25-, 26-, 29-, 30-Me), 1.01–1.74 (complex CH—, CH$_2$, 25H,); $^{13}$C NMR (CDCl$_3$) d 88.41, 79.38, 71.49, 55.77, 51.35, 47.07, 41.78, 40.99, 40.88, 40.87, 39.16, 37.52, 36.95, 36.51, 34.40, 34.18, 32.96, 29.08, 28.27, 27.57, 26.72, 26.72, 26.50, 24.82, 21.26, 18.54, 16.79, 15.96, 15.72, 13.82; MS (EI) 442, 424, 411, 371, 355, 303, 273, 257, 245, 231, 220, 207, 203, 189, 177, 162, 149, 135, 121, 107.

Example 19

Allobetulinlactone,
oleanan-3β-ol-28,19-β-lactone

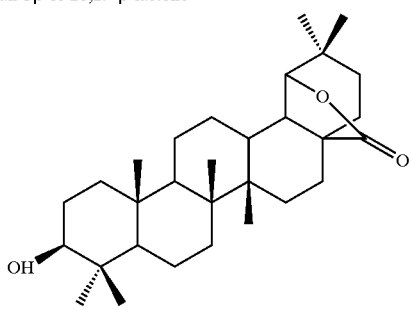

In 100-ml flask boil 2 g of Allobetulin-3-trifluoroacetyl lactone in 50 ml of $CH_3OH$ in presence of 0.723 g KOH for 4 hours. Evaporate methanol and dilute with 100 mL of cold water. Filter the precipitate and wash with water (3×50 mL). Dry crystals in oven at 110° C. and recrystallize from hexane-dichloromethane to yield white needles. mp. 316.3–317.6° C., IR (KBr) 3495, 2940, 2866, 1759, 1447, 1388, 1153, 1118, 967, 923 cm$^{-1}$; $^1$H NMR (CDCl$_3$) d 3.97 (S, 1H, 19H), 3.22 (DD, 1H, 3H), 1.057, 1.000, 0.987, 0.942, 0.903, 0.87, 0.791 (all S, 7×3H, 23-, 24-, 25-, 26-, 27-, 29-, 30-Me), 1.1–1.9 (complex CH—, CH$_2$—, 24H); $^{13}$C NMR (CDCl$_3$) d 180.207, 86.316, 79.174, 55.791, 51.528, 47.01, 46.413, 40.853, 40.212, 39.242, 39.177, 37.552, 36.313, 34.018, 33.843, 32.619, 32.232, 29.055, 28.254, 28.188, 27.642, 26.825, 25.842, 24.261, 21.178, 18.46, 16.85, 15.822, 15.669, 13.964; MS (EI) 456, 438, 423, 395, 356, 329, 261, 234, 206, 189, 175, 161, 147, 135, 121, 107, 95, 81, 69, 55, 43.

Example 20

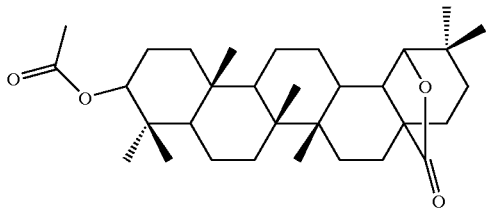

Allobetulinlactone-3-acetate
oleanan-28,19-β-lactone-3-acetate

In 100-ml flask stir 2 g of 3-O-acetyl-betulin in 50 ml of $CH_2Cl_2$ at 0° C. Add 10 ml of 99% proof $CF_3COOH$ stir for 10 minutes and after that add 2.2 g of powdered $NaBrO_3$. Stir the mixture for 6 hours and then pour in 100 ml of cracked ice and separate organic part. Extract with $CH_2Cl_2$ (3×10 ml) and wash combined organic extracts with 10% aqueous $NaHSO_3$ (2×30 ml), 5% aqueous $NaHCO_3$ (2×30 ml) and water (2×20 ml), and dry the extract over $Na_2SO_4$ (anh.). Evaporation of solvent gives 2.08 g of 3-O-acetyl allobetulin-lactone, which was recrystallized from hexane-dichloromethane to yield white needles. mp. 312.5–315.4° C. (dec.), IR (KBr) 2943, 2878, 1761, 1729, 1502, 1486, 1446, 1374, 1252 cm$^{-1}$; $^1$H NMR (CDCl$_3$) d 4.50 (DD, 1H, 3H), 3.94 (S, 1H, 19H), 2.03 (S, 3H, Ac—Me), 1.04, 0.97, 0.985, 0.8, 0.8, 0.79, 0.78 (all S, 7×3H, 23-, 24-, 24-, 25-, 26-, 29-, 30-Me), 1.02–1.79 (complex CH—, CH$_2$—, 23H); $^{13}$C NMR (CDCl$_3$) d 13.899, 15.779, 16.741, 16.879, 18.307, 21.164, 21.601, 23.896, 24.210, 26.745, 25.784, 28.158, 28.159, 29.004, 32.181, 32.568, 33.792, 33.916, 36.284, 37.428, 38.055, 38.878, 40.175, 46.420, 40.831, 46.959, 51.419, 55.835, 180.352, 81.244, 86.381, 171.579; MS (EI) 482, 438, 424, 395, 356, 327, 281, 253, 207, 189, 174, 162, 147, 135, 121, 43.

Example 21

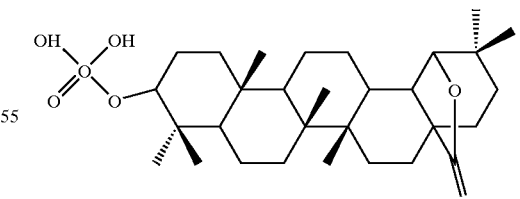

Allobetulinlactone-3-phosphate
oleanan-28,19-β-lactone-3-phosphate

In 100 mL round bottom flask boil a solution of allobetulin-3-phosphodichloride in 50 mL of dioxane and 1 mL of water for 18 hours. Dilute with cold water (50 mL) and filter white precipitate. Wash on filter with water (3×30 mL). Dry in oven (temperature not higher than 110° C.) to give 3.12 g of white crystalline compound mp. 226.7–230.1° C. (dec)[lit. ***], IR (KBr) 3414, 2945, 2868, 1760, 167, 1449, 1384, 1524, 1213, 1068, 1025, 967, 495 cm$^{-1}$; $^1$H NMR (CDC13/DMSOd6=1:1) d 5.64 (S, 2H, (OH)2) 3.94 (S, 1H, 19H), 3.81 (M, 1H, 3-H), 1.001, 0.98, 0.98, 0.89, 0.89, 0.87, 0.78 (all S, 7×3H, 23-, 24-, 25-, 26-, 27-, 29-, 30-Me), 1.05–1.95 (complex CH—, CH$_2$—, 23H); $^{13}$C NMR (CDCl$_3$/DMSOd6) d 177.852, 84,195, 82.504, 53.984, 49.510, 44.897, 44.431, 38.995, 38.405, 38.405, 37.275, 37.181, 35.556, 34.608, 32.065, 30.928, 30.243, 27.38, 26.637, 26.345, 24.851, 24.057, 23.758, 22.381, 19.408, 16.712, 15.174, 14.817, 14.059, 12.296; 31P NMR (D$_3$PO$_4$ 85% in D$_2$O) d-0.719.

Example 22

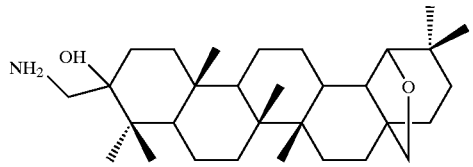

Allobetulin-3-hydroxy-3-aminomethyl
3-aminomethyl-3-hydroxy-28,19-β-epoxy-oleanan In 25 mL round bottom flask boil the mixture of allobelulon (0.86 g, 1.955 mmol), ZnI$_2$ (20 mg, 0.063 mmol) and tret-butyldimethylsilylcyanide (0.420 g, 3.78 mmol) in 15 mL of Toluene for 24 hours. Add the above mentioned mixture to a suspension of LiAlH$_4$ (0.37 g, 10 mmol) in 30 mL of THF drop wise and boil for 2 hours. Next, add 0.5 mL of concentrated KOH, dilute with 30 mL of THF and filter with diatomaceous earth. Dry over sodium sulfate and bubble HCl gas through the THF solution and filter the white precipitate (0.98 g). Dissolve the crystals in 50 mL of chloroform and wash with 1% NaHCO$_3$ until neutral reaction of universal paper indicator. Separate organic part and dry over sodium sulfate. Evaporation of solvent gives 0.89 g (96% yield) of white crystalline compound mp. 222.0–224.3° C., IR (KBr) 3414, 2939, 2868, 1617, 1461, 1384, 1036 cm$^{-1}$; $^1$H NMR (CDCl$_3$) d 3.67 (D, 1H, 28H, J=7.5 Hz), 3.521 (S, 1H, 19H), 3.437 (D, 1H, 28H, J=7.5 Hz), 2.95 (D, 1H, 31H, J=13.2 Hz), 2.757 (D, 1H, 31H, J=13.2 Hz), 2.523 (S, 3H, OH+NH$_2$), 0.972, 0.926, 0.911, 0.904, 0.894, 0.824, 0.798 (all S, 7×3H, 23-, 24-, 25-, 26-, 27-, 29-, 30-Me), 1.01–1.79 (complex CH—, CH$_2$—, 24H); $^{13}$C NMR (CDCl$_3$) d 88.13, 75.174, 71.428, 62.517, 53.554, 51.703, 47.018, 43.265, 41.669, 40.911, 40.882, 40.882, 37.683, 37.596, 36.933, 36.459, 34.309, 32.903, 30.265, 29.048, 27.416, 26.643, 26.454, 24.771, 24.166, 21.171, 19.947, 18.905, 17.076, 15.961, 13.811.

Example 22

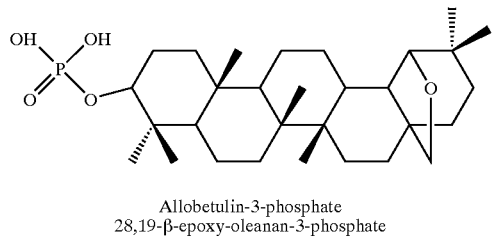

Allobetulin-3-phosphate
28,19-β-epoxy-oleanan-3-phosphate

In 100 mL round bottom flask boil a solution of Allobetulin-3-phosphodichloride in 50 mL of dioxane and 1 mL of water for 18 hours. Dilute with cold water (50 mL) and filter white precipitate. Wash on filter with water (3×30 mL). Dry in oven (temperature not higher than 110° C.) to give 3.12 g of white crystalline compound mp. 167.0–168.1° C. (dec), IR (KBr) 3469, 2947, 2868, 1775, 1467, 1388, 1221, 1169, 1022, 884, 585, 505, 481 cm$^{-1}$; $^1$H NMR; $^{31}$P NMR (D$_3$PO$_4$ 85% in D$_2$O) d-0.684.

Example 23

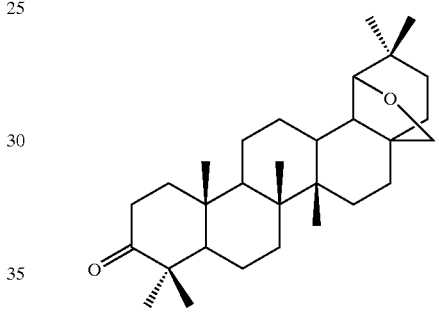

Allobetulon
oleanan-3-one-28,19-β-ether

In 100-mL round bottom two neck flask place 11 mmol (1.397 g) (COCl)$_2$ in 25 ml of dry CH$_2$Cl$_2$ at −50–60° C. (i—Pr alcohol—dry ice bath) and with efficient stirring add 22 mmol (1.76 g) of dry DMSO in 25 ml of dry CH$_2$Cl$_2$ in drop wise in 3–5 minutes. Stir the mixture for additional 5 minutes and then add crystals of allobetulin (10 mmol, 4.43 g), Stand solution for 30–45 minutes and after adding with 25 mmol (2.53 g) of triethylamine, remove cold bath and let temperature to increase up to 10° C. Pour the mixture in 100 ml of cracked ice, extract with CH$_2$Cl$_2$ (3×20 ml) and wash combined organic extracts with water (5×10 ml), 5% HCl (2×10 ml), and H$_2$O (2×10 ml). After drying over sodium sulfate solvent evaporation gives 4.4 g of crude compound, which after column chromatography (hexane:ether80:20) gives 4.31 g of white crystals mp. 228.8–233.1° C. [lit. 230–235° C.], IR (KBr) 2949, 2859, 1774, 1702, 1457, 1382, 1167, 1034 cm$^{-1}$; $^1$H NMR (CDCl$_3$) d 3.74 (D, J=10.3 Hz, 1H, 28-H), 3.48 (S, 1-H, 19-H), 3.39 (D, J=10.3 Hz, 1H, 28-H), 2.37 (M, 2H, 2-H,H), 1.85 (M, 1H, 19-H), 0.72, 0.81, 0.815, 0.91, 0.92, 0.99 (all S, 7×3H, 27-, 23-, 24-, 25-, 26-, 29-, 30-Me), 1.01–1.54 (complex CH—, CH$_2$, 25H); $^{13}$C NMR (CDCl$_3$) d 218.08, 88.01, 71.39, 55.08, 50.55, 47.43, 46.92, 41.60, 40.91, 40.68, 39.97, 37.11, 36.88, 36.43, 34.41, 34.23, 33.33, 32.86, 29.00, 26.92, 26.60, 26.60, 26.40, 24.73, 21.68, 21.16, 19.79, 16.52, 15.68, 13.63; MS (EI) 440, 422, 411, 369, 355, 281, 220, 207, 205, 191, 177, 163, 149, 135, 121.

Example 24

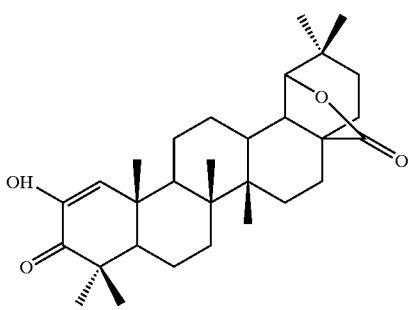

Allobetulonlactone-1-ene-2-ol
2-hydroxy-olean-1,2-ene-3-one-28,19-β-lactone

To a solution of Allobetulonlactone (1.0 g) in dry benzene-tert-butyl alcohol (1:1, 40 ml) was added a solution of potassium tert-butoxide (0.56 g) in tert-butyl (20 ml) and oxygen was bubbled into the stirred mixture for 3 hours. The mixture was acidified with 2.0 ml of glacial acetic acid and extracted with $CH_2Cl_2$. After washing with water (2×15 ml), 5% aqueous $NaHCO_3$ (2×30 ml) and water (30 ml), the extract was dried over $Na_2SO_4$ and evaporated to give crystals (m=0.983 g, 98%), which after chromatography on silica gel (hexane: ether40:60) yields a white crystalline compound mp. 238.8–243.6° C., IR (KBr) 3451, 2944, 2864, 1764, 1663, 1642, 1450, 1405, 1384, 1234, 1055, 967 cm$^{-1}$; $^1$H NMR (CDCl$_3$) d 6.47 (S, 1H, 2-H), 6.07–5.85 (1H, OH), 3.96 (S, 1H, 19H), 1.207, 1.153, 1.109, 1.037, 0.98, 0.974, 0.877 (all S, 7×3H, 23-, 24-, 25-, 26-, 27-, 20-, 30-Me), 1.05–1.91 (complex CH—, CH$_2$, 22H); $^{13}$C NMR (CDCl$_3$) d 201.36, 180.025, 144.217, 128.966, 86.192, 54.501, 46.879, 46.631, 46.376, 44.292, 41.654, 40.525, 38.936, 36.393, 33.836, 33.632, 32.568, 32.174, 29.034, 28.006, 27.365, 26.571, 25.784, 24.232, 21.841, 21.397, 20.923, 18.868, 16.282, 13.768, MS (EI) 468, 454, 441, 425, 407, 369, 340, 313, 303, 269, 259, 234, 215, 207, 189, 176, 165, 153, 151, 135, 128, 124, 108, 95, 78, 69, 55, 43.

Example 25

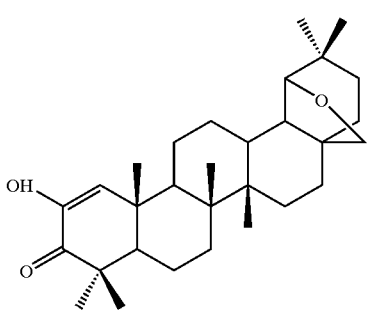

Allobetulon-1-ene-2-ol.
2-hydroxy-28,19-β-epoxy-olean-1(2)-ene-3-one

To a solution of allobetulon (1.8 g) in dry benzene-tert-butyl alcohol (1:1, 40 ml) was added a solution of potassium tert-butoxide (1.2 g) in tert-butyl (20 ml) and oxygen was bubbled into the stirred mixture for 1.5 hours. The mixture was acidified with 2.5 ml of glacial acetic acid and extracted with $CH_2Cl_2$. After washing with water (2×15 ml), 5% aqueous $NaHCO_3$ (2×30 ml) and water (30 ml), the extract was dried over $Na_2SO_4$ and evaporated to give crystals, which after chromatography on silica gel (hexane: ether= 85:15) 1402, 1234, 1058, 1035 cm$^{-1}$; $^1$H NMR (CDCl$_3$) d 6.46 (S, 1H, 1-H), 5.9 (S, 1H, 2-OH), 3.75 (D, 1H, 28H), 3.52 (S, 1H, 19-H), 3.52 (S, 1H, 28H), 0.78, 0.91, 0.99, 1.01, 1.09, 1.13, 1.19 (all S, 7×3, 23-, 24-, 25-, 26-, 27-, 29-, 30-Me), 1.05–1.78 (complex CH—, CH$_2$, 25H); $^{13}$C NMR (CDCl$_3$) d 201.43, 144.202, 129.29, 88.16, 71.523, 54.49, 46.99, 44.3, 41.75, 41.312, 38.97, 36.98, 36.56, 34.53, 33.83, 32.97, 29.1, 27.41, 26.6, 26.52, 24.86, 21.89, 21.51, 20.87, 18.96, 16.5, 13.64; MS (EI) 454, 383, 327, 281, 245, 215, 207, 191, 177, 151, 137, 136, 123, 109, 95, 81, 69, 55.

Example 26

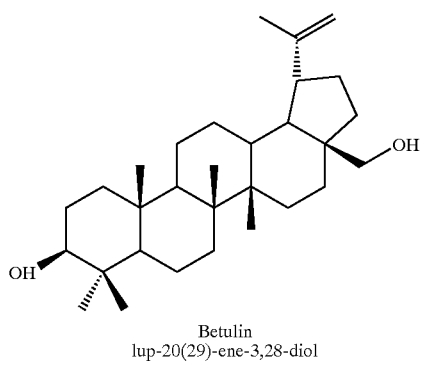

Betulin
lup-20(29)-ene-3,28-diol

Isolation of Betulin.

Betulin was isolated from paper birch (*B. papyrifera*) bark. Shredded, dry bark (500 g) has been extracted with chloroform on a Soxhlet apparatus for 10 hours. The extract was evaporated and then was left overnight at 5–7° C. Crystals were filtered and washed with hexane and then dried in oven to give 94.5 g of crude Betulin. Double crystallization from chloroform and then mixture of chloroform-isopropyl alcohol(4:1) gives 64–68 g of pure Betulin mp. 258–259° C. [lit. mp 256–261° C.]. IR (KBr) 3378, 2942, 2868, 1645, 1453, 1374, 1106, 1031,880 cm$^{-1}$; $^1$HNMR (CDCl$_3$) d 4.68 (S, 1H, 29-H), 4.58 (S, 1H, 29-H), 3.8 (D, J=10.3 Hz, 1H, 28-H, 3.34 (D, J=10.3 Hz, 1H, 28-H), 3.18 (DD, 1H, 3-H), 2.38 (M, 1H, 19-H), 1.68 (S, 3H, 30-Me), 0.76, 0.82, 0.97, 0.98, 1.02 (all S, 5×3H, 27-, 23-, 24-, 25-, 26-Me), 1.0–2.4 (complex CH—, CH$_2$, 25H,); $^{13}$C NMR (CDCl$_3$) d 151.249, 110.464, 79.736, 61.278, 56.017, 51.12, 49.48, 48.533, 48.534, 43.454, 41.647, 39.614, 39.432, 38.033, 37.894, 34.958, 34.725, 30.469, 29.901, 28.742, 28.123, 27.773, 25.929, 21.572, 19.845, 19.051, 16.879, 16.726, 16.136, 15.516; MS (EI) 442, 424, 411, 398, 393, 381, 288, 234, 207, 203, 189, 175, 161, 147, 135, 121, 107.

Example 27

Betulon-1-ene-2-ol.
lup-1(2),20(29)-diene-2,28-diol-3-one

To a solution of betulin-28-acetate (1.0 g) in dry benzene-tert-butyl alcohol (1:1, 40 ml) was added a solution of potassium tert-butoxide (1.05 g) in tert-butanol (20 ml). Oxygen was bubbled into the stirred mixture for 1.5 hours. The mixture was acidified with 2.2 ml of glacial acetic acid and extracted with CH₂Cl₂. After washing with water (2×15 ml), 5% aqueous NaHCO₃ (2×30 ml) and water (30 ml), the extract was dried over Na₂SO₄ and evaporated to give crystals, which after chromatography on silica gel (hexane:ether=80:20) yielded a white crystalline compound mp. 167–170 (dec) ° C., IR (KBr) 3446, 2944, 2870, 1717, 1669, 1647, 1457, 1406, 1237, 1032, 882 cm⁻¹; ¹H NMR (CDCl₃) d 6.43(S, 1H, 2-H), 6.12–5.81 (OH), 4.69 (S, 1H, 29H), 4.60 (S, 1H, 29H), 3.79 (DD, 1H, 28-H, J=10.7 Hz), 3.35 (DD, 1H, 28-H, J=10.7 Hz), 2.4 (M, 1H, 19-H), 1.69 (S, 3H, 30-Me), 1.203, 1.124, 1.105, 1.09, 0.976 (all S, 5×3H, 23-, 24-, 25-, 26-, 27-Me), 1.05–2.01 (complex CH—, CH₂ 22H); ¹³C NMR (CDCl₃) d 201.513, 150.491, 144.188, 129.228, 110.209, 60.768, 54.217, 48.883, 48.045, 48.045, 45.844, 44.278, 43.309, 42.019, 38.893, 37.654, 34.244, 34.149, 29.974, 29.398, 27.409, 27.226, 25.332, 21.907, 21.353, 20.457, 19.364, 19.021, 16.755 114.941; MS (EI) 454, 438, 424, 381, 325, 302, 271, 229, 215, 189, 177, 161, 135, 121, 95, 81, 55.

Example 28

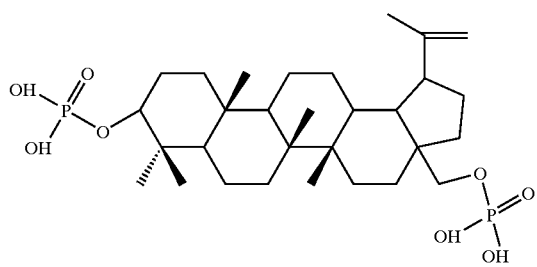

Betulin-3,28-diphosphaate
Lup-20(29)-ene-3,28-diphosphate

In 100 mL round bottom flask boil a solution of betulin-3, 28-diphosphodichloride in 50 mL of dioxane and 1 mL of water for 18 hours. Dilute with cold water (50 mL) and filtrate white precipitate. Wash on filter with water (3×30 mL). Dry in oven (temperature not higher than 110° C.).

Example 29

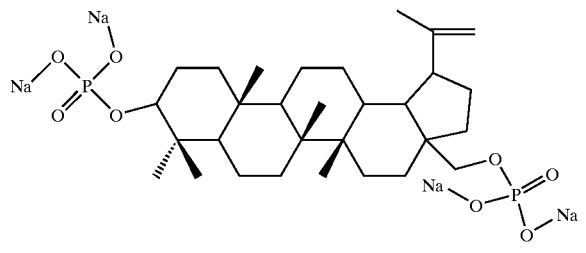

Betulin-3,28-diphosphate sodium salt
Lup-20(29)-ene-3,28-sodiumdiphosphate

In 100 mL round bottom flask to a suspension of 1 g (1.66 mmol) of betulin-3,28-diphosphate in 40 mL of water a solution of 0.6 g of sodium bicarbonate in 40 ml of water was added dropwise to maintain pH<=7. Water was evaporated under reduced pressure and white precipitate was dried in vacuum.

Example 30

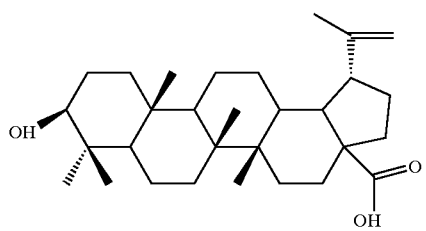

Betulinic acid
3-hydroxy-lup-20(29)-ene-28-oic acid

Betulinic aldehyde (1.5 g) was dissolved in 45 ml of ethyl acetate and then was placed in a 100 ml heatable column. 0.6 ml of distilled water and 23 mg of ABIN was added to the solution. Oxygen has been bubbled through the mixture at 50–60° C. for 6 hours with periodic addition of ABIN (5 mg per hour). Evaporation of solvent and following crystallization from MeOH gives 1.42 g of white crystals mp. 288–291° C. [lit. 291–292], IR (KBr) 3449, 2941, 2869, 1686, 1639, 1451, 1376, 1235, 1186, 1043, 886 cm⁻¹; ¹H NMR (CDCl₃), d 4.79 (S, 1H, 29H), 4.65 (S, 1H, 29H), 3.22 (DD, 1H. 3-H), 3.02 (T, 1H, 19H), 1.66 (S, 3H, 30-Me), 0.79, 0.83, 0.88, 1.0, 1.0 (all S, 5×3H, 23-, 24-, 25-, 26-, 27-Me), 1.05–2.24 (complex CH—, CH₂, 25H); ¹³C NMR (CDCl₃) d 180.403, 150.542, 109.86, 79.146, 56.433, 55.471, 50.64, 49.401, 47.025, 42.573, 40.824, 39.01, 38.842, 38.529, 37.348, 37.174, 34.456, 32.291, 30.688, 29.85, 28.138, 27.54, 25.631, 20.982, 19.518, 18.417, 16.282, 16.173, 15.495, 14.847; MS (EI) (after sililation) 518, 510, 487, 483, 471, 456, 428, 413, 393, 377, 353, 320, 306, 292, 257, 203,189, 175, 148,135, 129, 73.

Example 31

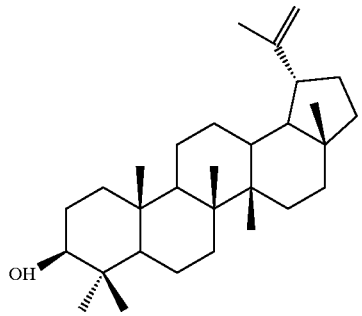

Lupeol,
monoglynol B,β-viscol, fagarasterol
lup-20(29)-ene-3β-ol

Combined parts after Betulin crystallization and solvent evaporation were separated on silica gel (eluent hex: ether= 10:1). After 150 ml solvent delay 20 fractions were collected. Fractions 1–7 contain mixture of lower terpenes, fractions 8–13 contained Lupeol mp 182.7–187.3° C., IR (KBr) 3380, 2920, 1450, 1405, 1025, 940 cm⁻¹; ¹H NMR (CDCl₃) d 4.69 (S, 1H, 29-H), 4.55 (S, 1H, 29-H), 3.18 (DD, 1H, 3-H), 2.35 (M, 1H, 19-H), 1.67 (S, 3H, 30-Me), 0.74, 0.76, 0.80, 0.92, 0.94, 1.01 (all S, 6×3H, 27-, 23-, 24-, 25-, 26-, 28-Me), 1.01–2.4 (complex CH—, CH₂, 25H,); ¹³C NMR (CDCl₃) d 151.32, 109.67, 79.32, 55.63, 50.77, 48.63, 48.33, 43.34, 43.17, 41.16, 40.34, 39.20, 39.04, 38.38, 37.50, 35.92, 34.61, 30.18, 28.33, 27.77, 26.09, 25.47, 21.26, 19.65, 18.65, 18.35, 16.46, 16.31, 15.72, 14.89; MS (EI) 426, 411, 393, 381, 369, 315, 281, 257, 218, 207, 189, 175, 161, 147, 135, 121, 107.

Example 32

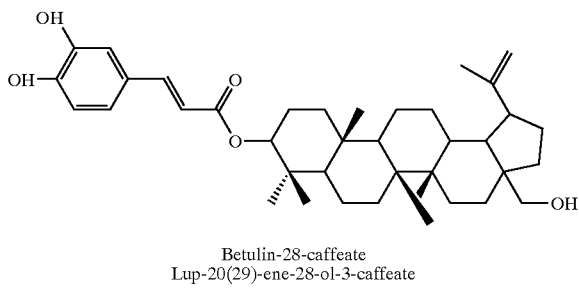

Betulin-28-caffeate
Lup-20(29)-ene-28-ol-3-caffeate

In a one liter round bottom one neck flask equipped with condenser a crude extract of outer birch bark (100 g) was dissolved in 500 ml of tetrahydrofuran. 10 g of aluminum triisopropoxide was added. The mixture was boiled for 1 hour, was allowed to cool to 45° C. This formed a precipitate, which was filtered and washed with tetrahydrofuran (5×40 ml) and dried on filter. Residual powder (34.2 g) was washed with 10% AcOH, dried on filter and extracted with 1% AcOH in isopropyl alcohol (5×50 ml). Combined extracts were concentrated in vacuum to 50 ml volume and diluted with water (200 ml) and filtered, and dried in vacuum at 40° C. The resulting 22.7 g of material was treated with a solution of diazomethane in diethyl ether and solvent was evaporated after no more nitrogen evolved. The remaining material was subjected for chromatography on silica gel (hexanes:ether=4:1) and 30 fractions were collected after 100 ml solvent delay and analyzed by TLC. Fractions 7, 8, 9 were combined and solvent was evaporated to give 4.78 g of lite-yellow crystals m.p. 191.1, 198.3° C., IR (KBr) 3426, 2945, 2871, 1708, 1678, 1630, 1604, 1514, 1447, 1376, 1273, 1181, 1109, 1012, 977 cm$^{-1}$; $^1$H NMR (CDCl$_3$), 7.602 (1H, DJ=15.9, C3'H from caffeate); 7.1 (1H, D, J=7.8, C2'-H from caffeate); 7.06 (1H, D, J=2); 6.86 (1H, DD, J=7.8, C5'H); 6.314 (1H, D, J=15.9); 4.68 (1H, S, 29-H); 4.62 (1H, M, C3H); 4.59 (1H, S, 29H); 3.82 (1H, D, J=11.5, 28H); 3.35 (1H, D, J=11.5, 28H), 1.69 (3H, S, 30-Me), 1.036, 0.991, 0.927, 0.899, 0.882 (5×3H, S, 23-, 24-, 25-, 26-, 27-Me); 1.05–2.24 (complex CH—, CH$_2$); $^{13}$C NMR (CDCl$_3$) 167.44, 151.29, 150.8, 149.47, 144.54, 127.82, 122.92, 116.83, 111.27, 110.06, 109.78, 81.141, 60.86, 56.28, 55.73, 50.62, 49.06, 48.11, 43.04, 41.264, 38.739, 38.39, 37.61, 37.42, 34.87, 34.30, 30.03, 29.47, 28.33, 27.35, 25.48, 24.165, 21.18, 19.39, 18.53, 17.03, 16.53, 16.31, 15.06.

Example 33

General Procedure for preparation of Betulin-3,28-dioxalate-polyethylenimine amids (samples 49–51, 100–106):

In 500 ml round bottom flask to a solution of polyethylenimine (MW$_{av}$ 600) (a mmol) in 100 ml of dichloromethane add a solution of Betulin-3,28-dioxalylchloride (b mmol) in 300 ml of dichloromethane drop wise while stirring at 21–23° C. The reaction mixture was then stirred for 15 minutes and dichloromethane was evaporated under reduced pressure at 40° C. Residue (oily amorphous material) was dried in vacuum.

49. Betulin-3,28-dioxalylchloride:polyethylenimine (MW$_{av}$ 600) ratio a:b=1:1;
50. Betulin-3,28-dioxalylchloride:polyethylenimine (MW$_{av}$ 600) ratio a:b=1:3;
51. Betulin-3,28-dioxalylchloride:polyethylenimine (MW$_{av}$ 600) ratio a:b=5:1;
100. Betulin-3,28-dioxalylchloride:polyethylenimine (MW$_{av}$ 600) ratio a:b=1:5;
101. Betulin-3,28-dioxalylchloride:polyethylenimine MW$_{av}$ 600) ratio a:b=3:1;
102. Betulin-3,28-dioxalylchloride:polyethylenimine (MW$_{av}$ 600) ratio a:b=1:10;
103. Betulin-3,28-dioxalylchloride:polyethylenimine (MW$_{av}$ 600) ratio a:b=1:1;
104. Betulin-3,28-dioxallhloride:polyethylenimine (MW$_{av}$ 600) ratio a:b=1:2;
105. Betulin-3,28-dioxalylchloride:polyethylenimine (MW$_{av}$ 600) ratio a:b=2:1;
106. Betulin-3,28-dioxalylchloride:polyethylenimine (MW$_{av}$ 600) ratio a:b=1:4.

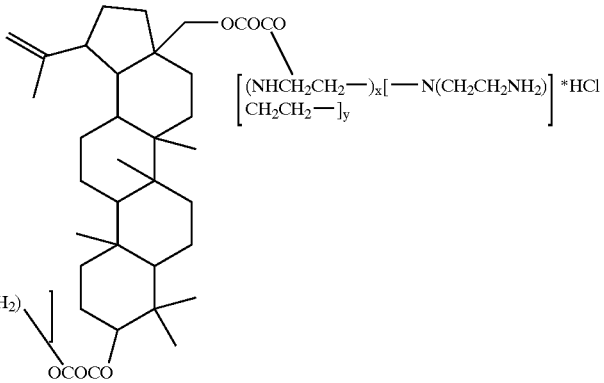

The compounds disclosed herein were tested for growth inhibition against four strains of bacteria: *Escherichia coli*, *Staphylococcus aureus*, methicillin-resistant *Staphylococcus aureus*, and *Bacillus subtilis*. These three species differ significantly in size, morphology, environment, and are evolutionarily distant. They represent three distinct genera. *E. coli* is a gram-negative, non-spore forming, rod-shaped, opportunistic pathogen that resides in the human digestive tract. *S. aureus* is a gram positive coccus, is usually found morphologically as a packet, and is an opportunistic human pathogen, often residing on or in the skin. *B. subtilis* is a gram positive spore-forming rod. Its native environment is the soil. The chemicals were tested for growth-inhibition of the bacteria by the Kirby-Bauer method. See, e.g.,

*Microbiology*, third edition; Lansing M. Prescott, John P. Harley, and Donald A. Klein; Wm. C. Brown Publishers.

Materials and Methods

Preparation of Media.

Mueller-Hinton agar (Difco Lab, Michigan) was prepared according to the manufacturer's directions, and 20 ml was dispensed in each sterile petri dish. Sterile nutrient broth (Difco Lab, Michigan) was also prepared according to the manufacturer's directions.

Growth of Organism.

Bacteria were grown in liquid nutrient broth for 18 hours at 37° C. until they were turbid.

Preparation of Plates.

An aliquot of 0.5 ml of cultured bacteria was aseptically transferred to the surface of a Mueller-Hinton agar plat, and spread using a cotton-tipped swab. Plates were then allowed to dry for 5 minutes. Then a 10 mm diameter filter paper disk impregnated with the test chemical was placed with sterile forceps on the plate. The disks were impregnated with 100 $\mu$l of a solution of the test compound in DMSO or in water, at the indicated concentrations in Table 1.

Determination of Susceptibility.

The zones of inhibition were measured after 18 hours growth at 37° C. Tests were done in triplicate.

Determination of Minimum Inhibitory Concentration.

Sterile tryptic soy broth was prepared according to the manufacturer's instructions (Difco Lab, Michigan). To each tube containing 7 ml of broth, test compounds dissolved in DMSO were added at different concentrations in triplicate. The tubes were incubated for 24 hours at 37° C. and then turbidity was measured using a calorimeter. The colorimeter was calibrated with sterile broth. The MIC was the lowest concentration that could prevent an increase in turbidity.

Results

Control disks impregnated with DMSO or 0.85% saline produced no zone of inhibition. Against *E. Coli*, betulin-3, 28-diphosphate, betulin-3,28-diglutarate, and betulin-3,28-didiglycolate were effective (Tables 1a and 1b). Each had a minimum inhibitory concentration of 0.282 $\mu$M (data not shown).

The compounds effective against *S. aureus* were betulin-3,28-dimaleate and betulin-3,28-diphthalate (Tables 1a and 1b). Each had a minimum inhibitory concentration of 2.3 $\mu$M.

Against methicillin resistant *S. aureus*, betulin-3,28-dimaleate was effective, with an MIC of 0.282 $\mu$M.

No compounds tested were effective against *Bacillus subtilis*.

Betulin-3,28-dimaleate was more effective against the laboratory strain (not methicillin resistant) *S. aureus* than streptomycin. In the disk diffusion assay, *S. aureus* was inhibited by 56 ng of betulin-3,28-dimaleate applied to the disk, while inhibition by streptomycin required 10 $\mu$g.

TABLE 1a

Effect of Betulin, Allobetulin, and Derivatives in DMSO Solution

| | | Zone of inhibition | | |
|---|---|---|---|---|
| Test Compound | Concentration mg/ml in DMSO | *Escherichia coli* | *Staphylococcus aureus* | *Bacillus subtilis* |
| Betulin | 1 mg/ml | 0 mm | 0 mm | 0 mm |
| Allobetulin | 1 mg/ml | 0 mm | 0 mm | 0 mm |
| Betulin 28-succinate | 1 mg/ml | 0 mm | 0 mm | 0 mm |
| Betulin 3,28-disuccinate | 1 mg/ml | 0 mm | 0 mm | 0 mm |
| Betulin 3,28-diphthalate | 10 mg/ml | 0 mm | 10.0 mm | 0 mm |
| Betulin 3,28-diglutarate | 10 mg/ml | 0 mm | 0 mm | 0 mm |
| Betulin 3,28-dimaleate | 10 mg/ml | 0 mm | 11.0 mm | 0 mm |
| Betulin 3,28-didiglycolate | 10 mg/ml | 0 mm | 0 mm | 0 mm |
| Allobetulin 3-succinate | 5 mg/ml | 0 mm | 0 mm | 0 mm |
| Allobetulin 3-glutarate | 1 mg/ml | 0 mm | 0 mm | 0 mm |
| Betulin 28-maleate | 10 mg/ml | 0 mm | 0 mm | 0 mm |
| Betulin 3,28-maleate | 20 mg/ml | 0 mm | 0 mm | 0 mm |
| Betulin 28-phthalate | 1 mg/ml | 0 mm | 0 mm | 0 mm |
| DMSO control | — | 0 mm | 0 mm | 0 mm |

TABLE 1b

Effect of Betulin, Allobetulin, and Derivatives in Water Solution

| Test Compound | Concentration ng/ml in water | Zone of inhibition | | |
|---|---|---|---|---|
| | | Escherichia coli | Staphylococcus aureus | Bacillus subtilis |
| Betulin 28-phthalate | 125 | 0 mm | 0 mm | 0 mm |
| Betulin 3,28-diglycine | 125 | 0 mm | 0 mm | 0 mm |
| Betulin ester | 125 | 0 mm | | |
| Betulin Di-(L-glutamic acid γ-benzyl ester) ester | 125 | 0 mm | 0 mm | 0 mm |
| Betulin dianiline ester | 125 | 0 mm | 0 mm | 0 mm |
| Betulin Di-(L-proline) ester | 125 | 0 mm | 0 mm | 0 mm |
| Allobetulin ethanol amine | 125 | 0 mm | 0 mm | 0 mm |
| Allobetulin 2-alanine ester | 125 | 0 mm | 0 mm | 0 mm |
| Allobetulin lactone | 125 | 0 mm | 0 mm | 0 mm |
| Lupeol | 125 | 0 mm | 0 mm | 0 mm |
| Lupeol-3-phthalate | 125 | 0 mm | 0 mm | 0 mm |
| Allobetulin glycine | 125 | 0 mm | 0 mm | 0 mm |
| Allobetulin 3-glutarate | 125 | 0 mm | 0 mm | 0 mm |
| Allobetulin ester | 125 | 0 mm | 0 mm | 0 mm |
| Allobetulin ethanolamine carbohydrate | 125 | 0 mm | 0 mm | 0 mm |
| Hederine hydrate | 0.5 | 0 mm | 0 mm | 0 mm |
| 3-Allobetulon-1-ene-2-succinate | 125 | 0 mm | 0 mm | 0 mm |
| Betulin arabinose galactan | 3.3 | 0 mm | 0 mm | 0 mm |
| Allobetulon-lactone-1-ene-2-ol | 125 | 0 mm | 0 mm | 0 mm |
| Betulin-3,28-diphenylalanine ester | 125 | 0 mm | 0 mm | 0 mm |
| Lupeol-3-succinate | 125 | 0 mm | 0 mm | 0 mm |
| Allobetulin 2-valine-ester | 125 | 0 mm | 0 mm | 0 mm |
| Allobetulin 3-phosphate | 125 | 0 mm | 0 mm | 0 mm |
| Allobetulin lactone phosphate | 125 | 0 mm | 0 mm | 0 mm |
| Allobetulin 3-phthalate | 125 | 0 mm | 0 mm | 0 mm |
| Betulon-1,2-ene-ol | 125 | 0 mm | 0 mm | 0 mm |
| Betulin 28-glutarate | 125 | 0 mm | 0 mm | 0 mm |
| Poly (ethylene glycol) bis (carboxymethyl) ester | 125 | 0 mm | 0 mm | 0 mm |
| Allobetulin-3-poly (ethylene glycol) bis (carboxymethyl) ether ester | 125 | 0 mm | 0 mm | 0 mm |
| Ursolic Acid | 125 | 0 mm | 0 mm | 0 mm |
| Betulin 3,28-diphosphate | 125 | 11.0 mm | 0 mm | 0 mm |
| Betulin 3,28-diglutarate | 125 | 12.0 mm | 0 mm | 0 mm |

TABLE 1b-continued

Effect of Betulin, Allobetulin, and Derivatives in Water Solution

| | | Zone of inhibition | | |
|---|---|---|---|---|
| Test Compound | Concentration ng/ml in water | Escherichia coli | Staphylococcus aureus | Bacillus subtilis |
| Betulin diglycolate | 125 | 10.0 mm | 0 mm | 0 mm |
| Allobetulon | 125 | 0 mm | 0 mm | 0 mm |
| 3β-Acetoxy-19αH-19,28 lactone oleanan | 125 | 0 mm | 0 mm | 0 mm |
| Pencillin G control | 10 units | 0 mm | 40.0 mm | 25.0 mm |
| Streptomycin control | 10 mcg | 20.0 mm | 15.0 mm | 24.0 mm |
| Tetracycline control | 30 mcg | 19.0 mm | 26.0 mm | 31.0 mm |

Example 34

Additional compounds were tested for activity against *E. coli*, laboratory strain *S. aureus* (not methicillin resistant), and *B. subtilis*. The compounds were tested by the disk diffusion method, as in Example 1, with application of a 10 mg/mil solution of the test compound in DMSO. The results are shown in Table 2.

*E. coli* was sensitive to betulin-3,28-diglycine, betulin-3-caffeate, and betulin-28-diglycolate. *S. aureus* was sensitive to betulin-3,28-di-L-valine, as well as to betulin-3,28-diphthalate. No compounds were found that inhibited *B. subtilis*.

TABLE 2

List of Compounds Tested Against Bacteria.

| S.No. Compound | Escherichia coli | Stapylococcus aureus | Bacillus subtilis |
|---|---|---|---|
| Allobetulin-3-succinate | x | x | x |
| Allobetulin lactone | x | x | x |
| Allobetulin lactone-3-acetate | x | x | x |
| Allobetulin-3-L-alanine ester | x | x | x |
| Allobetulin-3-L-valine ester | x | x | x |
| Allobetulin-3-L-proline ester | x | x | x |
| Allobetulin-3-diglycolate | x | x | x |
| Allobetulin-3-glutarate | x | x | x |
| Allobetulin-3-phthalate | x | x | x |
| Allobetulin-3-methylenamine | x | x | x |
| Allobetulin ethanolamine hydrochloride | x | x | x |
| Allobetulin-3-glycolate | x | x | x |
| Allobetulin-PEG-COOH Mw = 674 | x | x | x |
| Allobetulon lactone-1-en-2-succinate | x | x | x |
| Allobetulon-1-ene-2-ol | x | x | x |
| Allobetulon-1-ene-2-diglycolate | x | x | x |
| Betulin-3,28-diglycine ester | x | x | x |
| Betulin-28-glycine ester | x | x | x |
| Betulin arabinose galactan | x | x | x |
| Betulin-3,28-diglycine ester | o | x | x |
| Betulin-3-maleate | x | x | x |
| Betulin-3-28-Di-L-alanine ester | x | x | x |
| Betulin-3-28-diphenylalanine ester | x | x | x |
| Betulin-3,28-di-L-proline ester) | x | x | x |
| Betulin-3-caffeate | o | x | x |
| Betulin-3,28-di (3',3'-dimethyl) glutarate | x | x | x |
| Betulin-3,28-didiglycolate | x | x | x |
| Betulin-28-diglycolate | o | x | x |
| Betulin-3,28-diphthalate | x | o | x |
| Betulin-3,28-Di-L-phenylalanine ester | x | x | x |
| Betulin-3,28-Di-L-valine ester | x | o | x |
| Betulin-3,28-di-PEG-COOH Mw = 1448 | x | x | x |
| Betulin-3,28-di-PEG-COOH Mw = 906 crude | x | x | x |
| Allobetulin-3,28-(dipoly (ethylene glycol)bis (carboxymethyl) | x | x | x |

TABLE 2-continued

List of Compounds Tested Against Bacteria.

| S.No. Compound | Escherichia coli | Stapylococcus aureus | Bacillus subtilis |
|---|---|---|---|
| Lupeol | x | x | x |
| Lupeol succinate | x | x | x |
| Ursolic acid | x | x | x | x = compound tested
o = compound showed anti-microbial activity

Example 35

Derivatives of lupeol were tested for inhibition of bacterial growth using the Kirby-Bauer disk diffusion method and by growth in liquid culture. For the disk diffusion method, compounds were dissolved in DMSO and 100 µl was added to the 10 mm filter paper disk. The amount of compound applied to the disk varied. The amount applied for each compound was as follows: lupeol (50 µg), lupeol-3-maleate (15 µg), lupeol-3-thiodiglycolate (15 µg), lupeol-3-dimethyl succinate (60 µg), lupeol-3-phosphate (30 µg), lupenone (50 µg), lupenon-3-oxime (50 µg), lupeol-3-amine (50 µg), lupenon-1,2-ene-2-ol (50 µg). In liquid culture, the compounds were dissolved in DMSO at 1 mg/ml and then 100 µl was added to 7 ml of sterile broth, along with a ¹⁄₂₀₀ dilution of freshly grown bacterial liquid culture. The strains tested were *Staphylococcus aureus, Staphylococcus epidemidis*, and *Enterococcus faecalis*.

The results are shown in Tables 3 and 4.

TABLE 3

Antibacterial activities against *Staphylococcus aureus, Staphylococcus epidemidis,* and *Enterococcus faecalis* using the Kirby-Bauer disk diffusion method.

| Compounds in descending order of activity (amount applied to the disk) | Zone of inhibition (mm) against S. epiderm. | Compounds in descending order of activity | Zone of inhibition (mm) against S. aureus | Compounds in descending order of activity | Zone of inhibition (mm) against E. faecalis |
|---|---|---|---|---|---|
| Lupenon-1,2-ene-2-ol | 2.65 | Ampicillin | 6.1 | Ampicillin | 5.75 |
| Ampicillin | 2 | Chloramphenicol | 2.6 | Lupeol | 1.4 |
| Lupenone | 1 | Lupenone | 1.25 | Chloraphenicol | 1.25 |
| Lupeol-3-maleate | 0.5 | Streptomycin | 1.25 | Lupeol-3-maleate | 1.15 |
| Lupeol-3-thiodiglycolate | 0.5 | Lupeol | 1 | Lupeol-3-thiodiglycolate | 0.75 |
| Chloramphenicol | 0.5 | Lupenon-1,2-ene-2-ol | 0.85 | Lupeol-1,2-enc-2-ol | 0.6 |
| Lupeol | 0 | Lupeol-3-(3',3'-dimethyl)succinate | 0.5 | Lupenon oxime | 0.6 |
| Lupeol-3-(3',3'-dimethyl)succinate | 0 | Lupeol-3-phosphate | 0.5 | Lupenone | 0.5 |
| Lupeol-3-phosphate | 0 | Lupeol-3-maleate | 0.4 | Lupeol-3-phosphate | 0.5 |
| Lupenon oxime | 0 | Lupenon oxime | 0.4 | Lupeol-3-amine | 0.5 |
| Lupeol-3-amine | 0 | Lupeol-3-thiodiglycolate | 0.3 | Lupeol-3-(3',3'-dimethyl)succinate | 0 |
| Gentamicin | 0 | Lupeol-3-amine | 0.3 | Gentamicin | 0 |
| Streptomycin | 0 | Gentamicin | 0.1 | Streptomycin | 0 |

TABLE 4

Antibacterial activity against *Staphylococcus aureus, Staphylococcus epidermis,* and *Enterococcus faecilis* using optical density measurements. Optical density at 600 nm of bacteria in liquid culture was measured after growth for 24 hours in the presence of the test compound at 14 µg per ml

| Compounds in descending order of activity | Optical Density of S. epiderm | Compounds in descending order of activity | Optical Density of S. aureus | Compounds in descending order of activity | Optical Density of E. faecalis |
|---|---|---|---|---|---|
| Lupenon-1,2-ene-3-ol | 0.006 | Lupenon-1,2-ene-2-ol | 0.04 | Lupenon-1,2-ene-2-ol | 0.01 |
| Lupenone | 0.03 | Lupenone | 0.04 | Lupeol-3-maleate | 0.03 |
| Lupeol-3-thiodiglycolate | 0.035 | Lupeol | 0.06 | Lupeol | 0.03 |
| Lupeol | 0.04 | Lupeol-3-maleate | 0.06 | Lupeol-3-phosphate | 0.04 |
| Lupeol-3-maleate | 0.04 | Lupeol-3-thiodiglycolate | 0.06 | Lupeone | 0.04 |

TABLE 4-continued

Antibacterial activity against Staphylococcus aureus, Staphylococcus epidermis, and Enterococcus faecilis using optical density measurements. Optical density at 600 nm of bacteria in liquid culture was measured after growth for 24 hours in the presence of the test compound at 14 µg per ml

| Compounds in descending order of activity | Optical Density of S. epiderm | Compounds in descending order of activity | Optical Density of S. aureus | Compounds in descending order of activity | Optical Density of E. faecalis |
|---|---|---|---|---|---|
| Lupeol-3-(3',3'-dimethyl)succinate | 0.06 | Lupeol-3-(3',3'-dimethyl)succinate | 0.06 | Lupeol-3-amine | 0.04 |
| Lupeol-3-phosphate | 0.06 | Lupeol-3-phosphate | 0.06 | Lupeol-3-thiodiglycolate | 0.04 |
| Lupenon oxime | 0.06 | Lupeol oxime | 0.06 | Lupenon oxime | 0.45 |
| Lupeol-3-amine | 0.06 | Lupeol-3-amine | 0.06 | Lupeol-(3',3'-dimethyl)succinate | 0.07 |
| None | 0.07 | None | 0.08 | None | 0.85 |

The results with the disk diffusion method and by liquid growth were consistent with each other. Lupenon-1,2-ene-2-ol was the most active compound against almost all the bacteria, especially as measured in liquid growth. Lupenone also had excellent activity. Against S. epidermidis, lepeol-3-thiodiglycolate lupeol-3-maleate, and lupeol were active. Against S. aureus, all the tested compounds showed some activity. Against E. faecalis, all the compounds except lupeol-3-(3',3'-dimethyl)succinate showed activity.

The compounds shown to be active against at least one strain of bacteria in the assays above are the following: betulin-3-caffeate; betulin-3,28-diglutarate; betulin-28-diglycolate; betulin-3,28-diglycine; betulin-3,28-didiglycolate; bettlin-3,28-diphthalate; betulin-3,28-diphosphate; betulin-3,28-disuccinate; betulin-3,28-di-L-valine; lupeol; lupeol-3-amine; lupeol-3-(3',3'-dimethyl) succinate; lupeol-3-maleate; lupeol-3-phosphate; lupeol-3-thiodiglycolate; lupenone; lupenon-1,2-ene-2-ol; lupenon-3-oxime.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method of treating a mammal afflicted with a bacterial infection comprising administering to the mammal an effective anti-bacterial amount of a triterpene of formula (I):

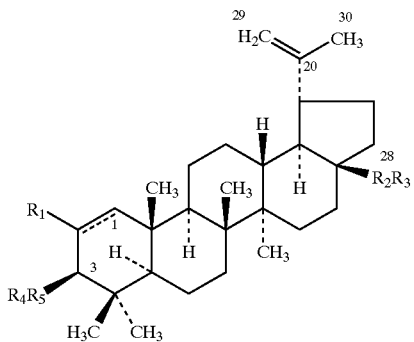

wherein $R_1$ is hydrogen or hydroxy;

$R_2$ is a direct bond, carbonyl, oxy, thio, carbonyl oxy, oxy carbonyl, $(C_6-C_{10})$aryl, or $(C_1-C_6)$alkyl;

$R_3$ is hydrogen, hydroxy, $(C_1-C_6)$alkyl, $O=P(OH)_2$, $O=P(OH)_2OP(O)(OH)$—, $(C_1-C_5)$alkanoyl, $Si(R)_3$ wherein each R is H, phenyl or $(C_1-C_6)$alkyl, $C(O)N(R)_2$, benzyl, benzoyl, tetrahydropyran-2-yl, 1-[$(C_1-C_4)$alkoxy]$(C_1-C_4)$alkyl, or a glycoside;

$R_4$ is hydrogen, hydroxy, $(C_1-C_6)$alkyl, $O=P(OH)_2$, $O=P(OH)_2OP(O)(OH)$—, $(C_1-C_5)$alkanoyl, $Si(R)_3$ wherein each R is H, phenyl or $(C_1-C_6)$alkyl, $C(O)N(R)_2$, benzyl, benzoyl, tetrahydropyran-2-yl, 1-[$(C_1-C_4)$alkoxy]$(C_1-C_4)$alkyl, a glycoside, or amino; or $R_4$ and $R_5$ together are oxo or (=NOH); and $R_5$ is direct bond, carbonyl, oxy, thio, carbonyl oxy, oxy carbonyl, $(C_6-C_{10})$aryl, or $(C_1-C_6)$alkyl; or $R_4$ and $R_5$ together are oxo or (=NOH);

wherein any alkyl can optionally be substituted with one or more halo, hydroxy, $(C_6-C_{10})$aryl, nitro, cyano, $(C_1-C_6)$alkoxy, trifluoromethyl, polyethyleneimine, poly(ethylene glycol), oxo, $NR_7R_8$, wherein $R_7$ and $R_8$ are each independently hydrogen, $(C_1-C_6)$alkyl or polyethyleneimine; —OP(=O)(OH)$_2$; or C(=O)OR$_9$, wherein $R_9$ is hydrogen, $(C_1-C_6)$alkyl, or polyethyleneimine;

each of the bonds represented by—is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, $(C_1-C_6)$alkoxy, trifluoromethyl, polyethyleneimine, poly(ethylene glycol), oxo, $NR_7R_8$, wherein $R_7$ and $R_8$ are each independently hydrogen, $(C_1-C_6)$alkyl or polyethyleneimine; or C(=O)OR$_9$, wherein $R_9$ is hydrogen, $(C_1-C_6)$alkyl, or polyethyleneimine;

or a pharmaceutically acceptable salt thereof.

2. The method of claim 1 wherein $R_4$ is not amino; $R_4$ and $R_5$ are not together (=NOH); and alkyl is not substituted with —OP(=O)(OH)$_2$.

3. The method of claim 1 wherein the bond between carbons 1 and 2 is a single bond.

4. The method of claim 1 wherein the bond between carbons 1 and 2 is a double bond.

5. The method of claim 1 wherein $R_1$ is hydrogen.

6. The method of claim 1 wherein $R_1$ is hydroxy.

7. The method of claim 1 wherein $R_2$ is a direct bond.

8. The method of claim 7 wherein $R_3$ is $(C_1-C_6)$alkyl; wherein any alkyl can optionally be substituted with one or more oxo, carboxy, amino, $(C_6-C_{10})$aryl, or —OP(=O)(OH)$_2$;

any alkyl is optionally interrupted on carbon with one or more oxy or thio;

any alkyl is optionally partially unsaturated; and any aryl can optionally be substituted with one or more hydroxy or carboxy.

9. The method of claim 8 wherein $R_3$ is 3-carboxypropenoyloxymethyl, aminoacetoxymethyl, (carboxymethoxy)acetoxymethyl, 4-carboxybutanoyloxymethyl, 2-carboxybenzoyloxymethyl, butanoyloxymethyl, or —CH$_2$OC(=O)OP(=O)(OH)$_2$.

10. The method of claim 1 wherein $R_4$ is $(C_1-C_6)$alkyl; wherein any alkyl can optionally be substituted with one or more oxo, carboxy, amino, $(C_6-C_{10})$aryl, or —OP(=O)(OH)$_2$, $(C_6-C_6)$aryl;

any alkyl is optionally interrupted on carbon with one or more oxy or thio;

any alkyl is optionally partially unsaturated; and any aryl can optionally be substituted with one or more hydroxy or carboxy.

11. The method of claim 1 wherein $R_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, —P(=O)(OH)$_2$, oxo, or (=NOH).

12. The method of claim 1 wherein $R_5$ is oxy or a direct bond.

13. The method of claim 1 wherein $R_1$ is hydrogen or hydroxy;

$R_2$ is a direct bond;

$R_3$ is $(C_1-C_5)$alkoxymethyl or hydroxymethyl;

$R_4$ is hydrogen, phosphono, sulfo, or $(C_1-C_6)$alkyl, and $R_5$ is oxy; or $R_4$ is amino and $R_5$ is a direct bond; or $R_4$ and $R_5$ together are oxo or (=NOH);

wherein any alkyl, or alkyl segment of an R group, is optionally interrupted on carbon with one or more oxy, thio, or imido;

wherein any alkyl, or alkyl segment of an R group, can optionally be substituted with one or more oxo, carboxy, amino, —OP(=O)(OH)$_2$, or phenyl;

wherein phenyl can optionally be substituted with one or more hydroxy or carboxy.

14. The method of claim 1 wherein $R_1$ is hydrogen or hydroxy;

$R_2$ is a direct bond;

$R_3$ is 3-carboxypropenoyloxymethyl, aminoacetoxymethyl, (carboxmethox)acetoxymethyl, 4-carboxybutanoyloxymethyl, 2-carboxybenzoyloxymethyl, butanoyloxymethyl, or

—CH$_2$OC(=O)OP(=O)(OH)$_2$;

$R_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, —P(=O)(OH)$_2$, oxo, or (NOH); and $R_5$ is oxy or a direct bond.

15. The method of claim 1 wherein the triterpene is betulin; betulin-3,28-diglycine; betulin-28-glycerol oxalate; betulin-28-glycine; betulin-28-oxalate; betulin arabinose galactan; betulin-3,28didiglycolate; betulin-3,28-diglycine; betulin-3-maleate; betulin-3,28-di-(L-glutamic acid γ-benzylester) ester; betulin-3,28-di-L-alanine; betulin-3,28-di-L-proline; betulin-3,28-dioxalate; betulin-1-ene-2-ol; betulin-3,28-diphenylalanine; betulin-3–28-dioxalate-polyethylene amine; betulin-3,38-diphosphate; betulin-3-caffeate; betulin-3,28-(3',3'-dimethyl) glutarate; betulin-28-diglycolate; betulin-28-glutarate; betulin-28-maleate; betulin-28-phthalate; betulin-3,28-di(3',3'-dimethyl) glutarate; betulin-3,28-didiglycolate; betulin-3,28-di (thiodiglycolate); betulin-3,28-diglutarate; betulin-3,28-dimaleate; betulin-3,28-diglycolate; betulin-3,28-diphthalate; betulin-3,28-di-L-phenylalanine; betulin-3,28—di-L-valine; betulin-28-succinate; betulin-3,28-disuccinate; betulin-3,28-di-(polyethylene glycol)-COOH (Mw=1448); betulin-3,28-di-(polyethylene glycol)-COOH (Mw=906 crude); betulin-3,28-di-(polyethylene glycol)-COOH (Mw=906 pure); betulinic acid; betulon-1-ene-2-ol; betulin-3,28-(dipoly(ethylene glycol)bis (carboxymethylester); allobetulin-3,28-(dipoly(ethylene glycol)bis (carboxymethyl allobetulin ester); hederin hydrate; lupeol; lupeol-3-glutarate; lupeol-3-succinate; lupeol-3-thiodiglycolate; lupeol-3-phthalate; oleanolic acid; ursolic acid; or uvaol.

16. The method of claim 1 wherein the triterpene is betulin; betulin-28-glycerol oxalate; betulin-28-oxalate; betulin arabinose galactan; betulin-3,28-didiglycolate; betulin-3,28-diglycine; betulin-3,28-di-(L-glutamic acid γ-benzylester) ester; betulin3,28-di-L-proline ester; betulin-3,28-dioxalate; betulin-1-ene-2-ol; betulin-3,28-dioxalate-polyethylene amine; betulin-3,28-diphosphate; betulin-3-caffeate; betulin-28-diglycolate; betulin-28-glutarate; betulin-28-maleate; betulin-28-phthalate; betulin-3,28-dithiodiglycolate; betulin-3,28-diglutarate; betulin-3,28-dimaleate; betulin-3,28-diglycolate; betulin-3,28-diphthalate; betulin-3,28-di-L-phenylalanine; betulin-di-L-valine; betulin-28-succinate; betulin-3,28-disuccinate; betulin-3,28-di-(polyethylene glycol)-COOH (Mw=906 pure); betulinic acid; betulon-1-ene-2-ol; betulin 3,28-(dipoly(ethylene glycol)bis (carboxymethylester); hederin hydrate; lupeol-3-glutarate; lupeol-3-succinate; lupeol-3-thiodiglycolate; lupeol-3-phthalate; oleanolic acid; uvaol.

17. The method of claim 1 wherein the triterpene is betulin-3-caffeate; betulin-28-diglycolate; betulin-3,28-diglutarate; betulin-3,28-diglycine; betulin-3,28-didiglycolate; betulin-3,28-dimaleate; betulin-3,28-diphosphate; betulin-3,28-diphthalate; betulin-3,28-di-L-valine; lupeol; lupeol-3-amine; lupeol-3-(3',3'-dimethyl) succinate; lupeol-3-maleate; lupeol-3-phosphate; lupeol-3-thiodiglycolate; lupenone; lupenon-1,2-ene-2-ol; lupenon-3-oxime.

18. The method of claim 1 wherein the bacterial infection is caused by *Escherichia coli, Staphylococcus sp., Enterococcus faecalis*, or a combination thereof.

19. The method of claim 18 wherein the bacterial infection is caused by *Staphylococcus aureus*.

20. A method of inhibiting or killing a bacterium, comprising contacting the bacterium with an effective antibacterial amount of a triterpene of formula (I):

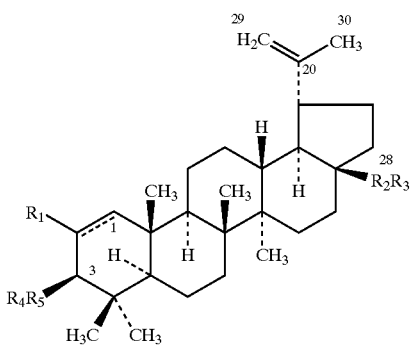

wherein

R$_1$ is hydrogen or hydroxy;

R$_2$ is a direct bond, carbonyl, oxy, thio, carbonyl oxy, oxy carbonyl, (C$_6$–C$_{10}$)aryl, or (C$_1$–C$_6$)alkyl;

R$_3$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, or a glycoside;

R$_4$ is hydrogen, hydroxy, (C$_1$–C$_6$)alkyl, O=P(OH)$_2$, O=P(OH)$_2$OP(O)(OH)—, (C$_1$–C$_5$)alkanoyl, Si(R)$_3$ wherein each R is H, phenyl or (C$_1$–C$_6$)alkyl, C(O)N(R)$_2$, benzyl, benzoyl, tetrahydropyran-2-yl, 1-[(C$_1$–C$_4$)alkoxy](C$_1$–C$_4$)alkyl, a glycoside, or amino; or R$_4$ and R$_5$ together are oxo or (=NOH); and R$_5$ is direct bond, carbonyl, oxy, thio, carbonyl oxy, oxy carbonyl, (C$_6$–C$_{10}$)aryl, or (C$_1$–C$_6$)alkyl; or R$_4$ and R$_5$ together are oxo or (=NOH);

wherein any alkyl can optionally be substituted with one or more halo, hydroxy, (C$_6$–C$_{10}$)aryl, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; —OP(=O)(OH)$_2$; or C(=O)OR$_9$, wherein R$_9$ is hydrogen, (C$_1$–C$_6$)alkyl, or polyethyleneimine;

each of the bonds represented by—is independently absent or is present;

wherein any alkyl is optionally interrupted on carbon with one or more oxy, thio, sulfinyl, sulfonyl, polyethyleneimine, or poly(ethylene glycol);

wherein any alkyl is optionally partially unsaturated;

wherein any aryl can optionally be substituted with one or more halo, hydroxy, nitro, cyano, (C$_1$–C$_6$)alkoxy, trifluoromethyl, polyethyleneimine, poly(ethylene glycol), oxo, NR$_7$R$_8$, wherein R$_7$ and R$_8$ are each independently hydrogen, (C$_1$–C$_6$)alkyl or polyethyleneimine; or C(=O)OR$_9$, wherein R$_9$ is hydrogen, (C$_1$–C$_6$)alkyl, or polyethyleneimine;

or a pharmaceutically acceptable salt thereof.

21. The method of claim 20 wherein R$_4$ is not amino; R$_4$ and R$_5$ are not together (=NOH); and alkyl is not substituted with —OP(=O)(OH)$_2$.

22. The method of claim 20, wherein the bond between carbons 1 and 2 is a single bond.

23. The method of claim 20 wherein the bond between carbons 1 and 2 is a double bond.

24. The method of claim 20 wherein R$_1$ is hydrogen.

25. The method of claim 20 wherein R$_1$ is hydroxy.

26. The method of claim 20 wherein R$_2$ is a direct bond.

27. The method of claim 26 wherein R$_3$ is (C$_1$–C$_6$)alkyl, wherein any alkyl can optionally be substituted with one or more oxo, carboxy, amino, (C$_6$–C$_{10}$)aryl, or —OP(=O)(OH)$_2$;

wherein any alkyl is optionally interrupted on carbon with one or more oxy or thio;

wherein any alkyl is optionally partially unsaturated;

wherein any aryl can optionally be substituted with one or more hydroxy or carboxy.

28. The method of claim 27 wherein R$_3$ is aminoacetoxymethyl, (carboxymethoxy)acetoxymethyl, 4-carboxybutanoyloxymethyl, 2-carboxybenzoyloxymethyl, 3-carboxypropanoyloxymethyl, butanoyloxymethyl, or —CH$_2$OC(=O)OP(=O)(OH)$_2$.

29. The method of claim 20 wherein R$_4$ is (C$_1$–C$_6$)alkyl, wherein any alkyl can optionally be substituted with one or more oxo, carboxy, ammo, (C$_6$–C$_{10}$)aryl, or —OP(=O)(OH)$_2$;

wherein any alkyl is optionally interrupted on carbon with one or more oxy or thio;

wherein any alkyl is optionally partially unsaturated;

wherein any aryl can optionally be substituted with one or more hydroxy or carboxy.

30. The method of claim 20 wherein R$_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, —P(=O)(OH)$_2$, oxo, or (=NOH).

31. The method of claim 20 wherein R$_5$ is oxy or a direct bond.

32. The method of claim 23 wherein

R$_1$ is hydrogen or hydroxy;

R$_2$ is a direct bond;

R$_3$ is (C$_1$–C$_6$)alkoxymethyl or hydroxymethyl;

R$_4$ is hydrogen, phosphono, sulfo, or (C$_1$–C$_6$)alkyl, and R$_5$ is oxy; or R$_4$ is amino and R$_5$ is a direct bond; or R$_4$ and R$_5$ together are oxo or (=NOH);

wherein any alkyl, or alkyl segment of an R group, is optionally interrupted on carbon with one or more oxy, thio, or imido;

wherein any alkyl, or alkyl segment of an R group, can optionally be substituted with one or more oxo, carboxy, amino, —OP(=O)(OH)$_2$, or phenyl;

wherein phenyl can optionally be substituted with one or more hydroxy or carboxy.

33. The method of claim 20 wherein

R$_1$ is hydrogen or hydroxy;

R$_2$ is a direct bond;

R$_3$ is aminoacetoxymethyl, (carboxmethox)acetoxymethyl, 4-carboxybutanoyloxymethyl, 2-carboxybenzoyloxymethyl, 3-carboxypropanoyloxymethyl, butanoyloxymethyl, or

—CH$_2$OC(=O)OP(=O)(OH)$_2$;

R$_4$ is 2-carboxybenzoyl, 2-amino-3-methylbutanoyl, 3-carboxypropenoyl, aminoacetyl, 4-carboxybutanoyl, (carboxymethoxy)acetyl, 3-(3,4-dihydroxyphenyl)propenoyl, carboxymethylenethioacetyl, 3-carboxy-3-methylbutanoyl, amino, —P(=O)(OH)$_2$, oxo, or (=NOH); and R$_5$ is oxy or a direct bond.

34. The method of claim 2 wherein the triterpene is betulin; betulin-3,28-diglycine; betulin-28-glycerol oxalate; betulin-28-glycine; betulin-28-oxalate; betulin arabinose galactan; betulin-3,28didiglycolate; betulin-3,28-diglycine; betulin-3-maleate; betulin-3,28-di-(L-glutamic acid-y-benzylester) ester; betulin-3,28-di-L-alanine; betulin-3,28-di-L-proline; betulin-3,28-dioxalate; betulin-1-ene-2-ol; betulin-3,28-diphenylalanine; betulin-3–28-dioxalate-polyethylene amine; betulin-3,38-diphosphate; betulin-3-caffeate; betulin-3,28-(3',3'-dimethyl) glutarate; betulin-28-diglycolate; betulin-28-glutarate; betulin-28-maleate; betulin-28-phthalate; betulin-3,28-di(3',3'-dimethyl) glutarate; betulin-3,28-didiglycolate; betulin-3,28-di (thiodiglycolate); betulin-3,28-diglutarate; betulin-3,28-dimaleate; betulin-3,28-diglycolate; betulin-3,28-diphthalate; betulin-3,28-di-L-phenylalanine; betulin-3,28-di-L-valine; betulin-28-succinate; betulin-3,28-disuccinate; betulin-3,28-di-(polyethylene glycol)-COOH (Mw=1448); betulin-3,28-di-(polyethylene glycol)-COOH (Mw=906 crude); betulin-3,28-di-(polyethylene glycol)-COOH (Mw= 906 pure); betulinic acid; betulon-1-ene-2-ol; 3,28 (dipoly (ethylene glycol)bis (carboxymethylester); 3,28 (dipoly (ethylene glycol)bis (carboxymethyl allobetulin ester); hederin hydrate; lupeol; lupeol-3-glutarate; lupeol-3-succinate; lupeol-3-thiodiglycolate; lupeol-3-phthalate; lupeol-3-succinate; oleanolic acid; ursolic acid; or uvaol.

35. The method of claim 23 wherein the triterpene is betulin; betulin-28-glycerol oxalate; betulin-28-oxalate; betulin arabinose galactan; betulin-3,28-didiglycolate; betulin-3,28-diglycine; betulin-3,28-di-(L-Glutamic acid r-benzylester) ester; betulin3,28-di-L-proline ester; betulin-3,28-dioxalate; betulin-1-ene-2-ol; betulin-3,28-dioxalate-polyethylene amine; betulin-3,28-diphosphate; betulin-3-caffeate; betulin-28-diglycolate; betulin-3,28-glutarate; betulin-28-maleate; betulin-28-phthalate; betulin-3,28-dithiodiglycolate; betulin-3,28-diglutarate; betulin-3,28-dimaleate; betulin-3,28-diglycolate; betulin-3,28-diphthalate; betulin-3,28-di-L-phenylalanine; betulin-di-L-valine; betulin-28-succinate; betulin-3,28-disuccinate; betulin-3,28-di-(polyethylene glycol)-COOH (Mw=906 pure); betulinic acid; betulon-1-ene-2-ol; betulin-3,28-(dipoly(ethylene glycol)bis (carboxymethylester); hederin hydrate; lupeol-3-glutarate; lupeol-3-succinate; lupeol-3-thiodiglycolate; lupeol-3-phthalate; oleanolic acid; uvaol.

36. The method of claim 20 wherein the triterpene is betulin-3-caffeate; betulin-28-diglycolate; betulin-3,28-diglutarate; betulin-3,28-diglycine; betulin-3,28-didiglycolate; betulin-3,28-dimaleate; betulin-3,28-diphosphate; betulin-3,28-diphthalate; betulin-3,28-di-L-valine; lupeol; lupeol-3-amine; lupeol-3-(3',3'-dimethyl) succinate; lupeol-3-maleate; lupeol-3-phosphate; lupeol-3-thiodiglycolate; lupenone; lupenon-1,2-ene-2-ol; lupenon-3-oxime.

37. The method of claim 20 wherein the bacterium is *Escherichia coli, Staphylococcus sp., Enterococcus faecalis,* or a combination thereof.

38. The method of claim 37 wherein the bacterium is *Staphyloccoccus aureus.*

39. The method of claim 20 wherein the contacting is in vitro.

40. The method of claim 20 wherein the contacting is in vivo.

* * * * *

UNITED STATES PATENT AND TRADEMARK OFFICE
CERTIFICATE OF CORRECTION

PATENT NO. : 6,689,767 B2
DATED : February 10, 2004
INVENTOR(S) : Krasutsky et al.

It is certified that error appears in the above-identified patent and that said Letters Patent is hereby corrected as shown below:

Title page,
Item [56], References Cited, OTHER PUBLICATIONS, "Koch, B. R. et al.," reference, after "XI-Duluth" insert -- Scientific Poster Exhibition, (Feb. 21, 2000), 1 page. --; and delete "Scientific Poster Exhibition, (Feb. 21, 2000), 1 page.".

Column 1,
Line 43, delete "," and insert -- . --, therefor.

Column 2,
Line 37, delete "R," and insert -- $R_5$ --, therefor.

Column 3,
Line 25, delete "–o–" and insert -- –O– --, therefor.
Line 47, delete "(Rf)" and insert -- ($R_f$) --, therefor.

Column 5,
Line 62, insert -- , -- before "or".

Column 9,
Line 37, delete "1,-pentenyl" and insert -- 1-pentenyl --, therefor.

Column 10,
Line 7, delete "4-carboxybutanoyloxymnethyl" and insert -- "4-caboxybutanoyloxymethyl" --, therefor.

Column 13,
Line 30, delete "(carboxmethoxy)" and insert -- (carboxymethoxy) --, therefor.

Column 14,
Line 3, delete "y-benzylester" and insert -- γ-benzylester --, therefor.
Line 3, delete "betulin3" and insert -- betulin-3 --, therefor.

Column 16,
Line 16, after "1" delete "below".

Column 21,
Line 26, after "10.03;" delete "0" and insert -- O --, therefor.

Column 22,
Line 13, delete "Useing" and insert -- Using --, therefor.

UNITED STATES PATENT AND TRADEMARK OFFICE
CERTIFICATE OF CORRECTION

PATENT NO.    : 6,689,767 B2
DATED         : February 10, 2004
INVENTOR(S)   : Krasutsky et al.

It is certified that error appears in the above-identified patent and that said Letters Patent is hereby corrected as shown below:

Column 23,
Line 1, delete "pyrrotidinone" and insert -- pyrrolidinone --, therefor.

Column 24,
Line 29, delete "1 mL" and insert -- 10 mL --, therefor.
Line 31, delete "(3'10 mL)" and insert -- (3x10 mL) --, therefor.
Line 37, after "4.57 (S, 1H) insert -- , --.
Line 47, delete "2succinate" and insert -- 2-succinate --, therefor.

Column 25,
Line 12, delete "(S 1H)" and insert -- (S, 1H) --, therefor.
Line 13, delete "(M 4H)" and insert -- (M, 4H) --, therefor.
Line 53, delete "CHCJ$_3$" and insert -- CHCl$_3$ --, therefor.

Column 26,
Line 33, delete "283,2" and insert -- 283.2 --, therefor.

Column 31,
Line 60, delete "500-mi" and insert -- 500-ml --, therefor.

Column 32,
Line 18, delete "0.06" and insert -- 1.06 --, therefor.
Line 51, delete "betalin" and insert -- betulin --, therefor.
Line 57, delete "128.77" and insert -- 1128.77 --, therefor.
Line 58, delete "(M 2H)" and insert -- (M, 2H) --, therefor.

Column 34,
Line 3, delete "26.825" and insert -- 26.826 --,therefor.
Line 38, delete "0.985" and insert -- 0.95 --, therefor.

Column 35,
Line 4, delete "cm$^1$" and insert -- cm$^{-1}$ --, therefor.
Line 37, delete "allobelulon" and insert -- allobetulon --, therefor.

Column 36,
Line 47, delete "," and insert -- . --, therefor.
Line 54, delete "(haxane:ether80:20)" and insert -- (hexane:ether=80:20) --, therefor.

Column 37,
Line 27, delete "(hexane: ether40:60)" and insert -- (hexane: ether=40:60) --, therefor.

UNITED STATES PATENT AND TRADEMARK OFFICE
CERTIFICATE OF CORRECTION

PATENT NO. : 6,689,767 B2
DATED : February 10, 2004
INVENTOR(S) : Krasutsky et al.

It is certified that error appears in the above-identified patent and that said Letters Patent is hereby corrected as shown below:

Column 38,
Line 37, delete "$^1$HNMR" and insert -- $^1$H NMR --, therefor.
Line 39, delete "28-H," before "3.34" and insert -- 28-H), --, therefor.
Line 41, delete "1.0- 2.4" and insert -- 1.01-2.4 --, therefor.

Column 39,
Line 18, after "16.755" insert -- , --.
Line 35, delete 'diphosphaate" and insert -- diphosphate --, therefor.

Column 42,
Line 24, insert -- ( -- before "$MW_{av}$".
Line 29, delete "dioxallhloride" and insert -- dioxalylchloride --, therefor.

Column 48,
Line 21, delete "mg/mil" and insert -- mg/ml --, therefor.
Table 2, line 2, delet "Stapylococcus" and insert -- Staphylococcus --, therefor.
Table 2, line 24, in "S.No.Compound", after "ester" delete ")".

Column 49,
Table 2, line 2, delete "Stapylococcus" and insert -- Staphylococcus --, therefor.

Column 49-50,
Table 3, line 7, in "Compounds in descending order of activity", delete "Lupeol-1,2-ene-2-ol" and insert -- Lupenon-1,2-ene-2-ol --, therefor.

Column 50,
Table 4, line 1, in "Compounds in descending order of activity", delete "Lupenon-1,2-ene-3-ol" and insert -- Lupenon-1,2-ene-2-ol --, therefor.
Table 4, line 7, in "Compounds in descending order of activity", delete "Lupeone" and insert -- Lupenone --, therefor.

Column 51,
Table 4, line 5, in "Compounds in descending order of activity", delete "Lupeol oxime" and insert -- Lupenon oxime --, therefor.
Line 33, delete "bettlin-3" and insert -- betulin-3 --, therefor.

Column 53,
Lines 7-8, delete "–OP(=O)(OH) $_2$;" and insert -- –OP(=O)(OH)$_2$; --, therefor.
Lines 25, delete "($_6$-C$_6$)aryl;" and insert -- (C$_6$-C$_{10}$)aryl; --, therefor.
Line 60, delete "(carboxmethox)" and insert -- (carboxymethoxy) --, therefor.

UNITED STATES PATENT AND TRADEMARK OFFICE
CERTIFICATE OF CORRECTION

PATENT NO. : 6,689,767 B2
DATED : February 10, 2004
INVENTOR(S) : Krasutsky et al.

It is certified that error appears in the above-identified patent and that said Letters Patent is hereby corrected as shown below:

Column 54,
Line 4, delete "(NOH)" and insert -- (=NOH) --, therefor.
Line 9, delete "betulin-3,28didiglycolate" and insert -- betulin-3,28-didiglycolate --, therefor.
Line 13, delete "betulin-3-28 dioxalate" and insert -- betulin-3,28-dioxalate --, therefor.
Line 37, delete "betulin 3" and insert -- betulin-3 --, therefor.

Column 56,
Line 33, delete "claim 23" and insert -- claim 20 --, therefor.
Line 36, delete "($C_1$-$C_6$)" and insert -- ($C_1$-$C_5$) --, therefor.
Line 54, delete "(carboxmethox)" and insert -- (carboxymethoxy) --, therefor.

Column 57,
Line 1, delete "claim 2" and insert -- claim 20 --, therefor.
Line 4, delete "betulin-3,28didiglycolate" and insert -- betulin-3,28-didiglycolate --, therefor.
Lines 5-6, ,therefor.
Lines 8, delete "betulin-3-28-dioxalate" and insert -- betulin-3,28-dioxalate --, therefor.
Line 9, delete "betulin-3,38-diphosphate" and insert -- betulin-3,28-diphosphate --, therefor.
Lines 22 and 23, delete "3,28" and insert -- betulin-3,28- --, therefor.
Line 28, delete "claim 23" and insert -- claim 20 --, therefor.
Line 32, delete "betulin3" and insert -- betulin-3 --, therefor.

Column 58,
Line 2, delete "betulin-3,28-glutarate" and insert -- betulin-28-glutarate --, therefor.

Signed and Sealed this

Eighth Day of June, 2004

JON W. DUDAS
*Acting Director of the United States Patent and Trademark Office*